United States Patent
Ferrante et al.

(10) Patent No.: US 11,993,098 B2
(45) Date of Patent: May 28, 2024

(54) WRITING INSTRUMENT, SYSTEM AND METHOD FOR TRANSPARENT MONITORING AND ANALYSIS OF WRITING

(71) Applicants: POLITECNICO DI MILANO, Milan (IT); UNIVERSITA' DEGLI STUDI DI MILANO, Milan (IT)

(72) Inventors: Simona Ferrante, Milan (IT); Alessandra Laura Giulia Pedrocchi, Milan (IT); Francesca Lunardini, Milan (IT); Davide Di Febbo, Milan (IT); Milad Malavolti, Milan (IT); Nunzio Alberto Borghese, Milan (IT)

(73) Assignees: POLITECNICO DI MILANO, Milan (IT); UNIVERSITA' DEGLI STUDI DI MILANO, Milan (IT)

(*) Notice: Subject to any disclaimer, the term of this patent is extended or adjusted under 35 U.S.C. 154(b) by 0 days.

(21) Appl. No.: 17/915,702

(22) PCT Filed: Mar. 30, 2021

(86) PCT No.: PCT/IB2021/052648
§ 371 (c)(1),
(2) Date: Sep. 29, 2022

(87) PCT Pub. No.: WO2021/198920
PCT Pub. Date: Oct. 7, 2021

(65) Prior Publication Data
US 2023/0126043 A1 Apr. 27, 2023

(30) Foreign Application Priority Data
Mar. 31, 2020 (IT) .................. 102020000006793

(51) Int. Cl.
*G06F 3/0354* (2013.01)
*B43K 29/08* (2006.01)

(52) U.S. Cl.
CPC .......... *B43K 29/08* (2013.01); *G06F 3/03545* (2013.01)

(58) Field of Classification Search
CPC ..................................................... G06F 3/03545
See application file for complete search history.

(56) References Cited

U.S. PATENT DOCUMENTS

| 5,562,104 A | 10/1996 | Hochberg et al. |
| 2004/0140962 A1 | 7/2004 | Wang et al. |

(Continued)

FOREIGN PATENT DOCUMENTS

| AT | 515 976 B1 | 1/2016 |
| AT | 520 751 B1 | 7/2019 |

(Continued)

OTHER PUBLICATIONS

International Search Report mailed Jun. 11, 2021, in corresponding to International Application No. PCT/IB2021/052648; 4 pages.

(Continued)

*Primary Examiner* — Sejoon Ahn
(74) *Attorney, Agent, or Firm* — Maier & Maier, PLLC

(57) ABSTRACT

A writing instrument that includes a writing element for depositing a writing material on a support and a plurality of sensors including at least a force sensor and a movement sensor, a communication unit that exchanges data with a remote device a control unit connected to the sensors and to the communication unit in order to transmit to the remote device the measurements provided by the sensors, a memory unit connected to the control unit that stores one or more measurements from the sensors; and a hollow casing that contains at least part of the writing element so that the writing end is exposed, and also houses the sensors, the control unit, the memory unit and the communication unit.

19 Claims, 10 Drawing Sheets

(56) References Cited

U.S. PATENT DOCUMENTS

| | | | |
|---|---|---|---|
| 2007/0246539 A1* | 10/2007 | Sandstrom | G06F 3/03545 |
| | | | 235/472.01 |
| 2007/0247445 A1* | 10/2007 | Lynggaard | G06F 3/0321 |
| | | | 345/179 |
| 2008/0094377 A1 | 4/2008 | Zander et al. | |
| 2009/0127006 A1* | 5/2009 | Lynggaard | G06F 3/03545 |
| | | | 178/19.01 |
| 2013/0060124 A1 | 3/2013 | Zietsma | |
| 2014/0073994 A1 | 3/2014 | Machado et al. | |
| 2018/0032159 A1 | 2/2018 | Pathak et al. | |
| 2019/0064942 A1* | 2/2019 | Ju | G06F 3/0386 |
| 2019/0064943 A1* | 2/2019 | Chang | G06F 3/03545 |
| 2019/0064947 A1* | 2/2019 | Saito | G06F 3/03545 |
| 2019/0065409 A1* | 2/2019 | Masi | G06F 3/0482 |

FOREIGN PATENT DOCUMENTS

| | | |
|---|---|---|
| DE | 10 2008 037487 A1 | 4/2010 |
| GB | 201008089 | 11/2011 |
| WO | 2007/003417 A2 | 1/2007 |

OTHER PUBLICATIONS

Written Opinion of the International Searching Authority mailed Jun. 11, 2021, in corresponding to International Application No. PCT/IB2021/052648; 8 pages.

Atilla Unlu et al: "Handwriting Analysis for Diagnosis and Prognosis of Parkinson's Disease", 2006, Biological and Medical Data Analysis Lecture Notes in Computer Science; Lecture Notes in Bioinformatics; LNCS, Springer, Berlin, DE, pp. 441-450, 10 pgs.

* cited by examiner

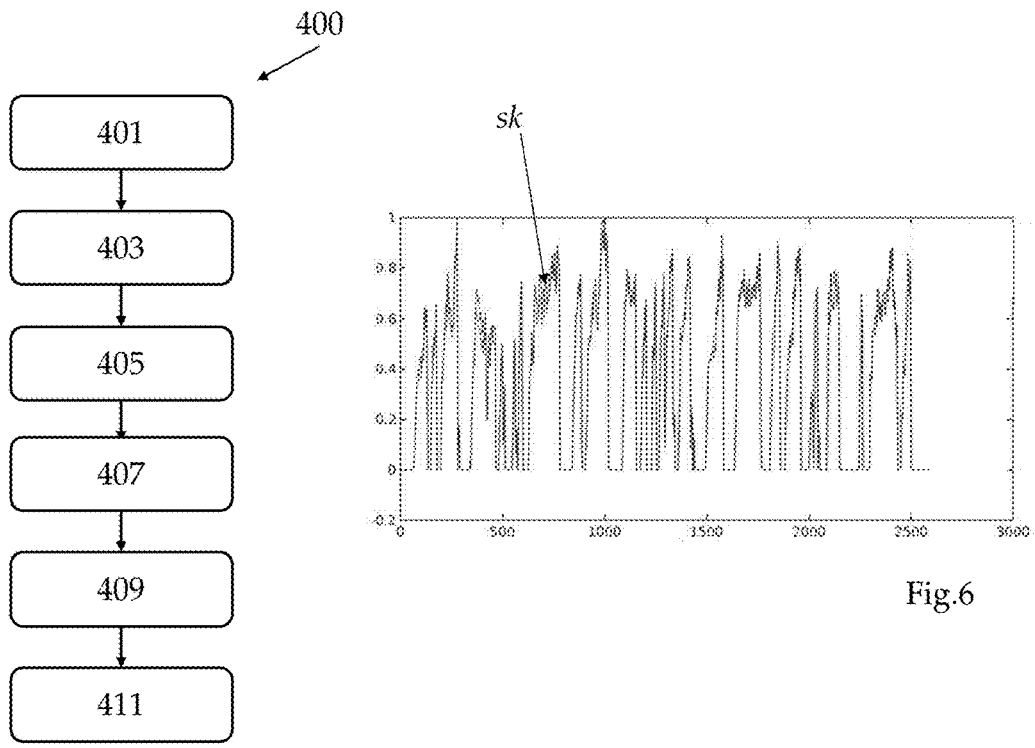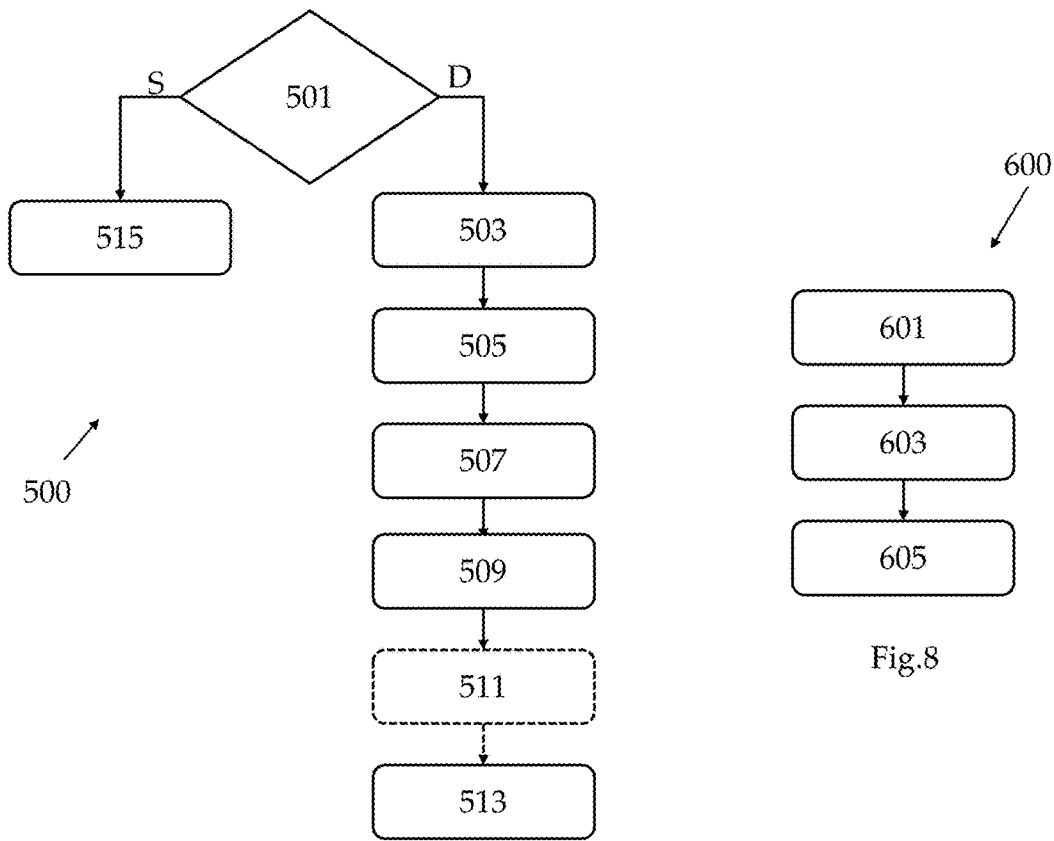

WRITING INSTRUMENT, SYSTEM AND METHOD FOR TRANSPARENT MONITORING AND ANALYSIS OF WRITING

TECHNICAL FIELD

The present invention relates to the sector of devices for analyzing human activities. In detail, the present invention relates to an instrument for acquiring data relating to the handwriting performed by an individual by means of said instrument. Furthermore, the present invention relates to a system and a method for monitoring and analyzing handwriting using said instrument.

BACKGROUND

Handwriting is a complex cognitive-motor operation that requires refined psychomotor abilities and extensive training. The possibility of analyzing the development of these abilities is considerably interesting from an academic medical point of view as it allows identifying and deepening the understanding on the establishment of manual, mental and visual coordination relationships that are necessary to perform fine manipulations, in general, and, in particular, the understanding on the processes and problems related to learning and production of handwriting.

Furthermore, the motor operations coordinated by the brain in combination with the neuromuscular and sensory systems—visual, proprioceptive and cutaneous ones—necessary for writing, can be subject to deterioration during old age and due to the onset of neurological diseases.

Devices designed to compensate for a tremor due to a neurological disease, for example Parkinson's disease, in order to obtain a legible written text have been proposed in the art.

For example, US 2018/032159 proposes a writing apparatus through which what a user writes by means of a stylus and on an electronic tablet is reproduced on paper. The data acquired through the interaction of the stylus on the electronic tablet while writing are used by the writing instrument to replicate a text written by the user on a sheet with increased readability.

Furthermore, methods for analyzing handwriting for the identification of neurological pathologies and cognitive decline of patients are known in the state of the art. Typically, such methods envisage carrying out handwriting tests under controlled conditions—i.e., according to specified protocols and prescribed acquisition methods—, during which the individual being examined is expected to copy a predetermined text or replicate a particular geometric shape, for example a spiral. These tests are usually performed by using special instrumentation including electronic pens and/or tablets.

For example, GB 201008089 proposes an apparatus for diagnosing a neurological disorder. The apparatus comprises a pen-like device and a sensorised writing surface. The device provides a first signal indicative of a force applied by at least one finger of the user while grasping the device. The writing surface provides a second signal indicative of the position of the device on the surface itself and/or a third signal indicative of a force with which the device is pressed on the surface. In addition, a video camera provides a fourth signal indicative of a position of part of the user's arm used for writing. The signals are compared with data relating to healthy subjects and subjects with pathologies and a probability that the user suffers from at least one neurological disorder is calculated.

WO 2007/003417 proposes a pen whose aim is to detect neuromotor information associated with a movement of a user's hand. The pen comprises a fluid-filled chamber having elastic walls, the internal pressure of this chamber corresponds to a force generated by the user's fingers grasping the pen. At least one pressure sensor is used to detect the liquid pressure and convert it into an electrical signal supplied to a control unit.

However, the execution of the tests and/or the conditions under which these tests are carried out can influence the individual being examined to the point that the information obtainable from the test itself can be altered. For example, the individual being examined may develop stress while taking the test accentuating inaccuracies and/or tremors or, conversely, the fact of being aware of being examined can lead the individual to pay more attention and show more commitment while taking the test with the possibility of attenuating or even masking pathological conditions.

Furthermore, these tests are performed for limited periods of time, therefore the examined data obtained from the observation of the individual are limited both in quantitative terms and in terms of a period of time of collection.

In addition, instruments are known for reproducing free-hand writing or drawing on a computer screen.

For example, US 2004/140962 discloses a writing instrument provided with an ink cartridge which allows writing normally and with one or more inertial sensors for measuring the movement of the instrument. The instrument also comprises a memory for recording movement measures and a transceiver for transferring measurements to a computer in order to reproduce images representative of the signs written by a user by means of the writing instrument.

Although the instrument proposed in US 2004/140962 allows reproducing what a user has written on a screen, it is not suitable for obtaining information suitable for analyzing the presence or the onset of a neurological pathology in a transparent way for a user.

SUMMARY

An object of the present invention is to overcome the disadvantages of the prior art.

In particular, an object of the present invention is to provide a writing instrument, such as a pen, an infinite pencil, a pop-a-point pencil, a marker, etc., which allows monitoring the handwriting of an individual in a transparent way with respect to the latter. In particular, with 'transparent' it is intended without restrictions either on the content, or on the writing method (e.g. block letters, italics), or on the way of holding the instrument by the individual being examined, or on the place where it is supposed to be written (for example in the vicinity of an acquisition instrument). Furthermore, 'transparent' also means that the user does not interact with the writing instrument to activate/deactivate the monitoring of the or to transfer the data obtained from such monitoring to a computer.

Furthermore, said writing instrument is substantially indistinguishable from a common writing instrument.

A further object of the present invention is to propose a writing instrument which allows monitoring the handwriting of an individual for prolonged periods of time, in particular, with no need for intervention by qualified operators.

Furthermore, the writing instrument allows it to be used for prolonged periods, i.e. it is not necessary to make frequent energy recharges.

A further object of the present invention is to present a system and a method for analyzing handwriting which allows identifying alterations in the handwriting of an individual indicative of the onset of a neurodegenerative pathology or other neuromotor disorder. In particular, this object is achieved with no need for protocols to be imposed either for the calibration of the instrument or for writing particular words, phrases or symbols.

A further object of the present invention is to present a system and a method for analyzing handwriting which allows recognising the movement of the writing instrument indicative of a learning disorder of an individual, typically a school-age child.

A further object of the present invention is to present a system and method for analyzing handwriting capable of identifying one or more symbols written by an individual.

These and other objects of the present invention are achieved by a system incorporating the features of the annexed claims, which form an integral part of the present description.

According to a first aspect, the present invention is directed to a writing instrument comprising:
- a writing element comprising a writing end configured for depositing a writing material on a support;
- a plurality of sensors comprising at least:
  - a force sensor configured to measure a force applied to said writing element, and
  - a movement sensor configured to measure movement of the instrument in a three-dimensional space;
- a communication unit configured to exchange data with a remote device via a wireless communication channel;
- a control unit connected to the plurality of sensors and to the communication unit configured to control said plurality of sensors and said communication unit in order to transmit to the remote device the measures of the sensors in presence of a connection between the communication unit and the remote device,
- a memory unit connected to the control unit and configured to store one or more measures provided by said plurality of sensors, and
- a hollow casing configured to contain at least partially said writing element, so as to leave the writing end of the writing element exposed through a first end of the casing, and to contain completely said plurality of sensors, the control unit, the memory unit and the communication unit.

Advantageously, the control unit is further configured:
- to detect a condition of lack of connection between the communication unit and the remote device,
- in such a condition of lack of connection, to detect writing measures corresponding to movement measures having a value greater than a threshold, and
- to store the writing measures if, within a predetermined period of time, the control unit detects a number of writing measures greater than a predetermined number.

Thanks to this solution, it is possible to ensure that the measurements detected by the sensors on board the writing instrument are made available and transmitted in a reliable way, limiting or completely eliminating the loss of useful information and, at the same time, limiting the energy consumption by the electronics on board the writing instrument. Furthermore, the acquisition of measurements and the transmission of data are transparent for the individual being examined, and avoiding any form of stress deriving from being aware of being examined right at that instant. In particular, in the event of failed connection with the remote device, the writing instrument automatically stores only measurements that, due to their amplitude, can be associated with writing movements, excluding those movements that may be involuntary or not connected to handwriting. By storing the writing measures even when the connection with the remote device is not available, the instrument can be used transparently by the monitored patient, who does not need to remember to have the instrument connected to the remote device.

This solution is very effective in unsupervised monitoring of an individual's handwriting. Thanks to the fact that the casing completely encloses and hides the sensors and electronics of the writing instrument, the instrument is substantially indistinguishable from a common corresponding writing instrument, for example an, infinite, pen, a pop-a-point pencil, a marker, etc., so as not to influence the way the individual uses it. In other words, the interaction of the individual with the writing instrument is natural and the operation of writing or, more generally, of drawing a sign is familiar. Furthermore, the instrument does not impose constraints on how it must be grasped or used, so as to allow to the individual a handwriting as spontaneous as possible, in particular, the individual is not required to press or interact directly with interface elements, detection elements and/or calibration elements while writing. These characteristics therefore allow to acquire data that substantially are not influenced by specific test conditions, thus allowing an ecological, transparent analysis and not disturbed by the system for measuring the writing abilities of the individual being examined.

In one embodiment, the control unit is further configured for:
- detecting a first writing measure
- activating the communication unit when said first writing measure is detected, and
- transmitting in real time the measurements provided by the plurality of sensors, when the connection is established between the communication unit and the remote device before a maximum time has lapsed from the activation of the communication unit.

Thanks to this solution, it is possible to activate the communication unit promptly when the acquisition of the information relating to the use of the instrument by a user is possible.

Preferably, the control unit is further configured to transmit in real time the measurements provided by the plurality of sensors only when the control unit detects a number of writing measures greater than said predetermined number.

In this way the data transmission can be limited to the actual uses of the instrument by the user, obtaining a more efficient energy consumption.

In one embodiment, the control unit is further configured for:
- activating the communication unit when said first writing measure is detected;
- when a connection is established between the communication unit and the remote device, receiving a memorization command transmitted by the remote device, and storing the measurements provided by the plurality of sensors in the memory unit, in response to the reception of the memorization command transmitted by the remote device.

Thanks to this configuration, it is possible to guarantee a reliable and adequate recording of the measurements in order to carry out accurate analysis on the use of the instrument even if an insufficient quality of connection to ensure a correct data transmission is detected by the remote device. Again this solution allows controlling in a simple and effective way the start of the acquisition of the measurements under controlled conditions, for example during the execution of a test.

In one embodiment, the control unit is further configured to deactivate the communication unit while storing the measurements provided by the plurality of sensors in the memory unit;
when a reduction of the writing measure below the threshold is detected, stop the storage of the measurements in the memory unit, and activate the communication unit to exchange data with the remote device.

Preferably, the control unit is further configured for:
deactivating the communication unit when a connection is not established between the communication unit and the remote device before a maximum time has elapsed since the activation of the communication unit;
waiting for a waiting period, and reactivating the communication unit to exchange data with a remote device.

Thanks to these solutions it is possible to reduce the energy consumption of the instrument so as to guarantee a high autonomy.

In one embodiment, the control unit is further configured for:
activating the communication unit when said first writing measure is detected;
when a connection is established between the communication unit and the remote device, receiving a real-time data transmission command from the remote device, and sending in real time to the remote device the measurements provided by the plurality of sensors, in response to the reception of the streaming command transmitted by the remote device.

This solution allows the writing instrument to be used as a tracker for exergames or for supervised evaluations of handwriting carried out in an environment and/or under controlled conditions.

In one embodiment, the control unit is configured to sample at least the measurements provided by the movement sensor with a sampling frequency equal to or greater than 30 Hz, preferably equal to or greater than 50 Hz.

These sampling values make it possible to acquire the information on the modalities of writing or, more generally, of use of the instrument that is necessary to recognise indications of a neurological pathology or a learning disorder. In particular, sampling frequencies with a frequency equal to or greater than 50 Hz make it possible to clearly recognise a tremor while using the instrument.

In one embodiment, the movement sensor is housed in a position having a shorter distance from a second end of said casing with respect to a distance from the first end thereof, said second end of the casing being opposite to the first end. Preferably, said distance is calculated with respect to a main length direction of the writing instrument.

In a preferred embodiment, the movement sensor is housed at a second end of said casing, said second end of the casing being opposite to the first end.

Thanks to this structure, the arrangement of the sensors within the writing instrument is particularly advantageous. In particular, the distance between the movement sensor and the writing end of the writing element makes it possible to detect minimal movement variations of the writing instrument. In addition, the force sensor is capable of detecting minimal variations in the pressure applied by the individual on a support.

In one embodiment, the force sensor is associated with a terminal end of the writing element, said terminal end being opposite to the writing end.

This arrangement of the force sensor is particularly simple and makes it possible to effectively measure the force associated with the pressure of the writing instrument when the latter is resting on the support.

In one embodiment, the movement sensor comprises at least one among:
a linear acceleration sensor configured to provide a measure of an acceleration of the instrument along a predetermined direction,
an angular velocity sensor configured to measure a rotation speed of the instrument in a predetermined plane, and a magnetometer.

Preferably, the movement sensor comprises an inertial measurement unit.

Thanks to this solution, it is possible to obtain a complete set of information on the movement of the writing instrument during the writing operations performed by the individual being examined, which can be processed to identify various information, even of a complex type, on the writing abilities of the individual being examined and, more generally, on the psychomotor abilities of the individual being examined.

In one embodiment, the casing comprises a separable first portion and a second portion. Preferably, the first portion and the second portion comprise corresponding mating apertures transverse to a main direction of the casing. In particular, the first portion is configured to house said writing element, while the second portion is configured to house the plurality of sensors, the control unit, the memory unit and the communication unit.

Preferably, the second portion of the casing is configured to completely hide the plurality of sensors, the control unit, the memory unit and the communication unit housed therein from the user's view.

This structure of the writing instrument allows the writing element to be replaced in an extremely simple way once it is exhausted. Consequently, the writing instrument can be used by the individual being examined for particularly long periods of time, not limited by the amount of material stored in the writing element.

Furthermore, this structure makes it possible to avoid the user interacting with the electronics on board the writing instrument. Finally, this compact structure allows minimizing the internal wiring between the electronics components on board the writing instrument, in particular between the control unit and the force and movement sensors.

In a particularly advantageous embodiment, further comprises a power supply unit which can be selectively connected at least to the control unit to provide electric energy thereto.

Furthermore, the casing comprises a first portion, a second portion and a third portion which can be separated one from the other. The first portion is configured to removably house at least part of said writing element, while the second portion is configured to house the plurality of sensors, the control unit, the memory unit and the communication unit. Finally, the third portion comprises: a first element removably fastened to the first portion, and a second element removably fastened to the second portion.

The first element and the second element are slidingly coupled so as to slide between a first position, in which the writing end of the writing element is contained within the first portion, and a second position, in which the first portion and the first element of the third portion move towards the second portion thereby exposing the writing end of the writing element at the first end of the casing.

Furthermore, the first element comprises a conductive component configured to contact a pair of electrical contacts connected to the power supply unit and protruding from the second portion towards the first element of the third portion, when the first element and the second element are in the second position, the contact between the pair of electrical contacts and the conductive component allowing the supply of electrical energy at least to the control unit.

Preferably, the second element of the third portion comprises:
- a coupling end to the second portion,
- a free end opposite the coupling end,
- a through hole between the free end and the coupling end, the through hole being shaped to receive the writing element and to hold a terminal end of the writing element, opposite the writing end, at the coupling end, and
- at least one pin projecting in a direction transverse to the length direction of the through hole.

Furthermore, the first element of the third portion comprises:
- a coupling end to the first portion,
- a free end opposite the coupling end,
- a through hole between the free end and the coupling end, the through hole being configured to at least partially receive the second element of the third portion,
- a helical groove formed in a wall that delimits said through hole, the groove being adapted to receive said pin of the second element so as to guide a rotation of the first element with respect to the second element during the sliding between the first position and the second position, and vice versa,
- a shoulder portion at the free end and facing the second portion, the shoulder portion being configured to house the conductive component.

Even more preferably, the conductive component comprises a sheet of electrically conductive material and wherein the electrical contacts are of the pogo pin type.

The structure of the writing instrument proposed above allows the electronic components to be powered only when the instrument is actually used for writing, thus obtaining a substantial extension of the device's autonomy, in a completely transparent manner for the user, i.e. without the user having to actively interact with the electronic components of the instrument.

In one embodiment, the writing element is selected from:
an ink pen refill;
a core of an infinite pencil;
a core of a pop-a-point pencil, and
a stick made in porous material soaked in ink.

In other words, the writing instrument can be made according to different needs, in particular, related for example to the abilities and/or age of the individual to be examined.

A different aspect of the present invention relates to a system for monitoring and analyzing handwriting comprising a writing instrument according to any one of the previous embodiments and a processing device, said processing device in turn comprising:
- a communication module configured to exchange data with the communication unit of the writing instrument, and
- a processing module configured to process the data provided by the writing instrument and providing an indication relating to at least one symbol written with the writing instrument.

This system makes it possible to exploit the data collected by the writing instrument in an effective and transparent way for the individual being examined. In particular, the data provided by the sensors can be exploited to perform various analyses on the use of the writing instrument by the user.

In fact, in one embodiment, the processing device is configured to extract indicators on the onset of neurological pathologies, such as tremor, from the measures provided by the sensors. In a completely independent way—and in addition or as an alternative to the extractions of indicators—the processing device can be configured to identify the symbols written by the user by means of the writing instrument. More generally, the processing device can be configured to identify the movement in space and time of the writing end of the writing instrument.

A further aspect of the present invention relates to a writing analysis method, implemented by the system described above. Said method comprises the steps of:
- determining a static disturbance in the force measures provided by the force sensor of the plurality of sensors of the writing instrument;
- subtracting said static disturbance from the force measures provided by the force sensor;
- processing the force measures provided by the force sensor by means of an algorithm for removing the baseline;
- converting to a null value, each measured value lower than a threshold value, and
- identifying a sequence of force measures different from zero as a single continuous writing movement performed through the writing instrument.

In this way it is possible to identify in a simple and reliable way single continuous writing movements, or strokes, which allow obtaining a particularly accurate and precise analysis of the writing abilities of the individual being examined.

In one embodiment, the method further comprises the steps of:
- determining a variation frequency of the movement measures provided by the movement sensor, and
- when said variation frequency is greater than a threshold value:
  calculating a tilt angular velocity of the writing instrument on the basis of angular velocity measures included in the movement measures provided by the movement sensor;
  calculating a further tilt angular velocity of the writing instrument on the basis of linear acceleration measures included in the measures of movement provided by the movement sensor, and
  calculating an adjusted tilt angular velocity of the writing instrument as a linear combination of the tilt angular velocity and of the further tilt angular velocity of the writing instrument.

Preferably, the step of calculating an adjusted tilt angular velocity of the writing instrument as a linear combination of the tilt angular velocity and of the further tilt angular velocity of the writing instrument comprises calculating the adjusted tilt angular velocity as:

$$(\hat{\vartheta}k_1\hat{\vartheta}_g + k_2(\hat{\vartheta}_a - \hat{\vartheta})),$$

where $\hat{\vartheta}_y$ is the tilt angular velocity determined on the basis of angular velocity measures, $\hat{\vartheta}_a$ is the tilt angle determined based on the further tilt angular velocity of the writing instrument based on the linear acceleration measures, $k_1$ is a constant parameter comprised between 1.2 and 1.7, preferably equal to 1.5, and $k_2$ is a constant parameter comprised between 0.3 and 0.6, preferably equal to 0.4.

In addition or alternatively, when said variation frequency is equal to or less than a threshold value,
it comprises:
calculating the tilt angle of the writing instrument as:

$$\vartheta = \sin^{-1}\left(\frac{a_z}{g}\right),$$

where $a_z$ is an acceleration measure aligned to a main direction of the writing instrument and g is the acceleration of gravity. Preferably, said measure is provided by the accelerometer aligned to the main direction of the writing instrument and g is the acceleration of gravity.

This way of calculating the variation rate of the tilt angle allows to accurately evaluate the movement of the writing instrument. In particular, this method makes it possible to compensate for errors in the calculation of the tilt angle at high frequencies, where significant accelerations introduce non-negligible errors in the calculation of the same tilt angle. Therefore, it is possible to perform a particularly accurate analysis of the movement of the writing instrument during the writing operations performed by the individual being examined.

Further features and advantages of the present invention will be more apparent from the description of the accompanying drawings.

BRIEF DESCRIPTION OF THE DRAWINGS

The invention will be described below with reference to some examples, provided for explanatory and non-limiting purposes, and illustrated in the accompanying drawings. These drawings illustrate different aspects and embodiments of the present invention and, where appropriate, reference numerals illustrating similar structures, components, materials and/or elements in different figures are indicated by similar reference numbers.

FIG. 1b is a simplified exploded view of the writing instrument of FIG. 1a;

FIG. 5 is a flowchart illustrating a procedure for identifying sequences of continuous writing, or strokes, by a processing device of the system of FIGS. 3a and 3b according to an embodiment of the present invention;

FIG. 6 is a graph of a function of the force detected by the writing instrument as a function of time;

FIG. 7 is a flowchart illustrating a procedure for identifying symbols written by means of the writing instrument by a processing device of the system of FIGS. 3a and 3b according to an embodiment of the present invention;

FIG. 8 schematically illustrates the organization of the information on handwriting collected by the system of FIGS. 3a and 3b according to an embodiment of the present invention;

DETAILED DESCRIPTION OF THE EMBODIMENTS

Figure 1A:
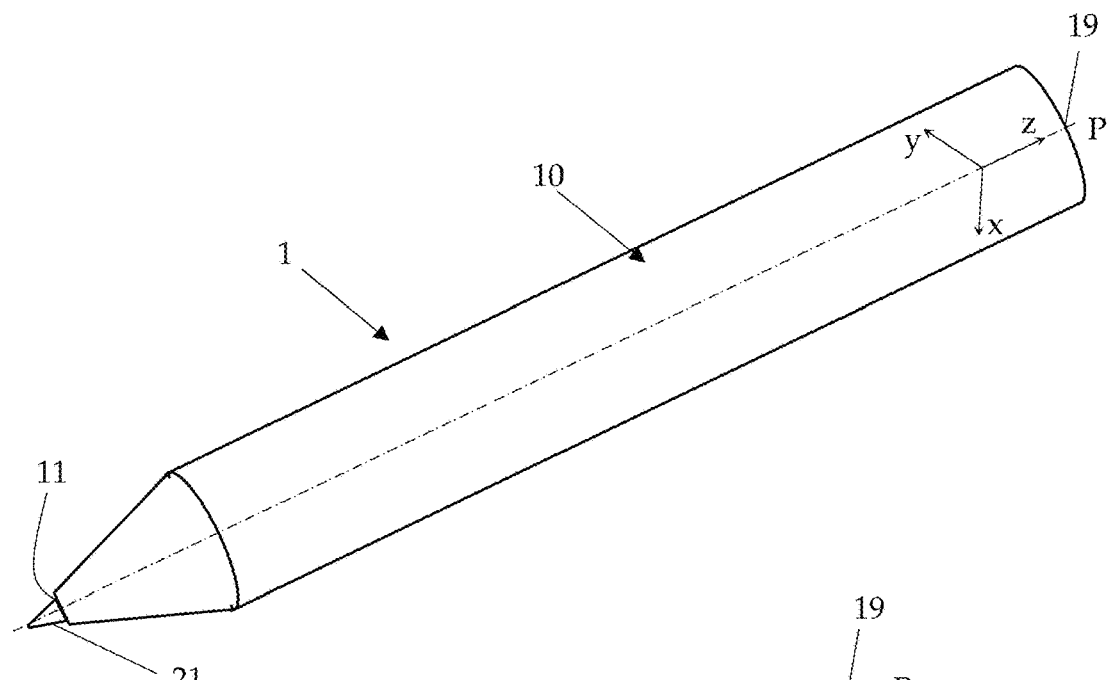
FIG. 1a illustrates a schematic axonometric view of a writing instrument according to an embodiment of the present invention.

While the invention is susceptible to various modifications and alternative constructions, certain preferred embodiments are shown in the drawings and are described hereinbelow in detail. It is in any case to be noted that there is no intention to limit the invention to the specific embodiment illustrated, rather on the contrary, the invention intends covering all the modifications, alternative and equivalent constructions that fall within the scope of the invention as defined in the claims.

The use of "for example", "etc.", "or" indicates non-exclusive alternatives without limitation, unless otherwise indicated. The use of "includes" means "includes, but not limited to" unless otherwise stated.

Figure 1B:
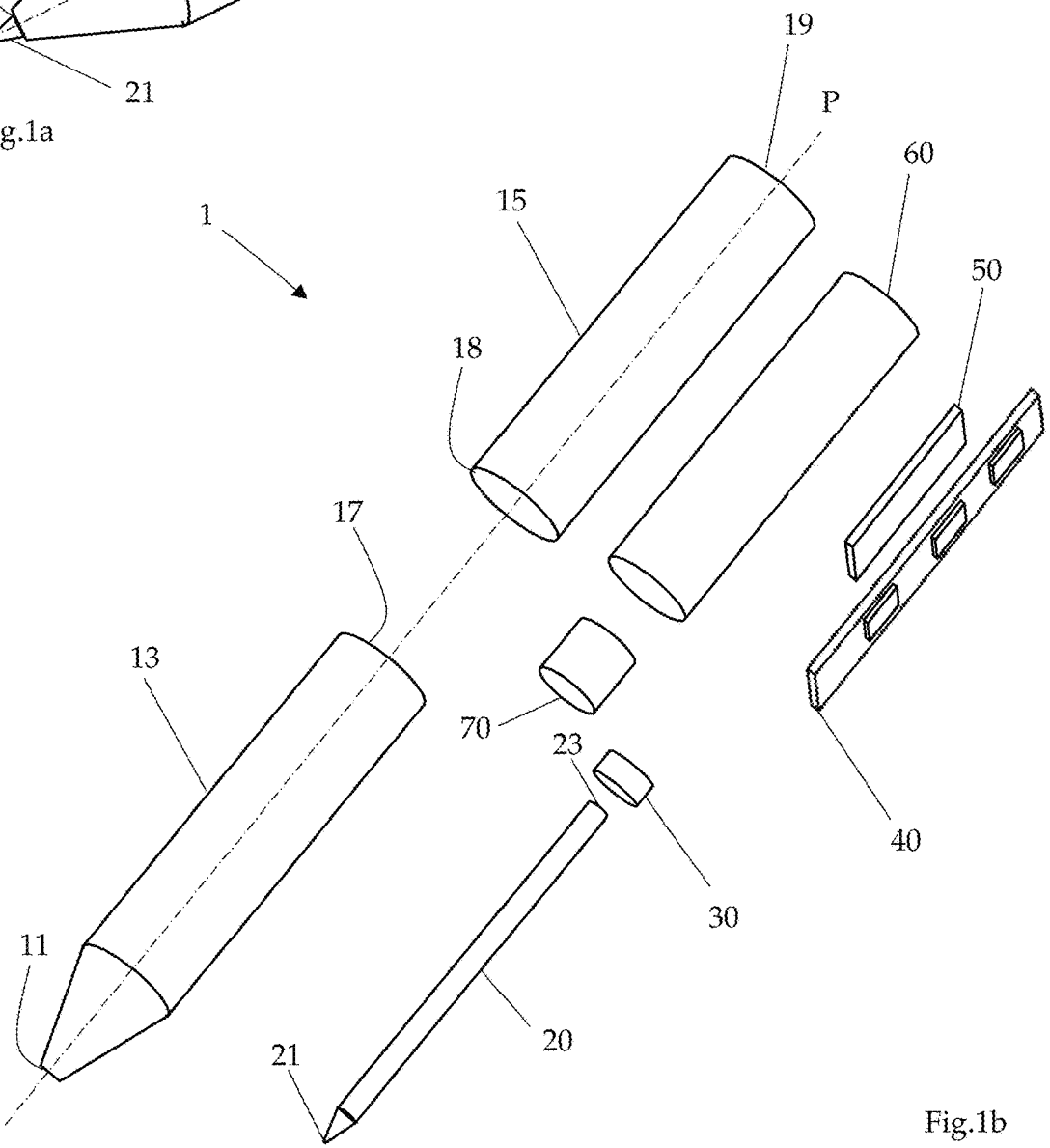

With reference to FIGS. 1a and 1b, a writing instrument, a ballpoint pen 1 in the example considered are described according to an embodiment of the present invention.

The pen 1 comprises a casing 10, a writing element 20—also called refill—, a force sensor 30, preferably a load cell, an electronic module 40, a battery 50 and preferably, a shell 60 and a support element 70.

In the embodiment considered, the casing 10 is configured to house the other elements of the pen 1. For this purpose, the casing is hollow and comprises an aperture at a first end 11 to allow a corresponding writing end 21 of the writing element 20 to protrude from the casing 10 and to allow handwriting, i.e. the release of a quantity of ink, in the example considered, on a surface, for example a sheet of paper. Preferably, the casing 10 is shaped so that the writing element 20 is substantially coaxial to an axis of symmetry of the casing 10 when the writing end protrudes from the casing 10 through the corresponding aperture. Even more preferably, the writing element 20 coupled to the casing 10 is substantially aligned and superimposed on a main direction P of the pen 1.

In the example considered, the casing comprises two portions 13 and 15 which can be removably coupled to each other. The first portion 13 is configured to house the writing element 20 and comprises the first end 11 in order to allow the writing end to protrude outside the casing 10. The second portion 15 is configured to house the remaining elements of the pen 1, in particular, the electronic module 40, the battery 50 and the force sensor 30.

Furthermore, each portion 13 and 15 comprises a respective aperture 17 and 18, respectively. Each aperture allows access to a cavity defined by the respective portion 13 and 15, and is provided with corresponding coupling elements (not shown in the schematic drawing of FIG. 1b), for example a thread and a counter-thread, bayonet coupling elements or snap coupling elements, etc.

In the example considered, the shell 60 is substantially a hollow cylinder of suitable dimensions for fitting the cavity defined by the second portion 15 of the casing 10 to size. The shell 60 is configured to receive inside it the electronic module 40 and the battery 50. Preferably, the shell 60 is also configured to engage with the support element 70 at the aperture 18 of the second portion 15 of the casing 10 when the shell 60 is inserted therein. For example, a portion of the shell 60 is shaped to receive a corresponding shaped portion of the support element 70. Alternatively, the shell 10 and the support element 70 comprise coupling elements of one of the types described above in relation to the coupling elements of the apertures 17 and 18.

The support element 70 is configured to house the force sensor 30 so that the force sensor 30 remains in contact with a terminal end 23 of the writing element 20—opposite the writing end 21 of the same—when the elements of pen 1 are assembled. Furthermore, the support element 70 is configured to allow an electrical connection between the force sensor 30 and the electronic module 40. Finally, the force sensor 30 is held in position by the support element 70 so as to measure forces substantially aligned to the main direction P of the pen 1.

Figure 2:
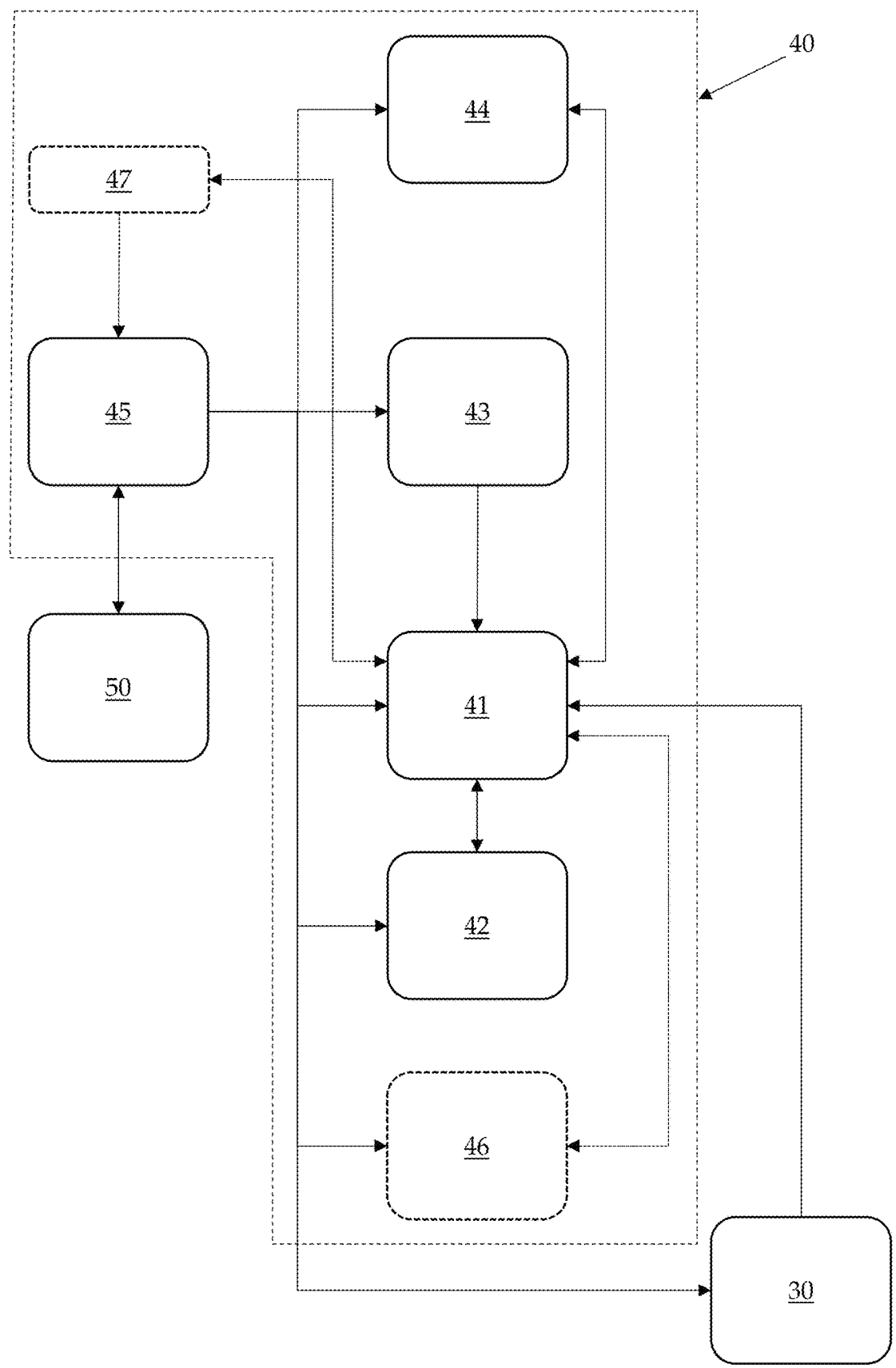
FIG. 2 is a block diagram of the electronics on board the writing instrument of FIGS. 1a and 1 b.

With particular reference to the block diagram of FIG. 2, the electronics on board the pen 1 is now described in greater detail. In the example considered, the electronic module 40 comprises a control unit 41—for example, comprising one or more of a microprocessor, a micro controller, an ASIC, an FPGA, a DSP and/or another element capable of processing data—, a memory 42—preferably, both volatile and non-volatile—, a movement sensor, preferably an IMU 43 (acronym for Inertial Measurement Unit), a radio frequency communication unit, preferably a BLE unit 44 (acronym for BlueTooth Low Energy). For example, the IMU 43 comprising at least two accelerometers and a vertical gyroscope. More preferably, the IMU 43 comprises a three-dimensional accelerometer and a three-dimensional gyroscope, for example the IMU 43 can be implemented by a module of the iNEMO family by ST Microelectronics, for example an LSM6DSM module.

The electronic module 40 further comprises a power unit 45 connected to the battery 50 and to the other units of the electronic module for supplying electrical energy to the same. Optionally, the electronic module 40 may comprise a user interface 46—for example from a simple LED to a complex system provided with input/output elements—and/or a connector 47 to allow charging the battery 50 and/or the transfer of data from/to the control unit 41. Preferably, the connector 47 is accessible through an aperture (not shown in the Figures) provided in the casing 10, for example at the end of the casing 10 opposite the end from which the writing end 21 of the writing element 20 of the pen 1 comes out.

The control unit 41 is connected to the force sensor 30 and to the IMU 43, to receive measurements of relative physical quantities detected by them, to the memory 42, to store data and access data stored therein, and to the BLE 44, for control the activation and data transmission thereof, but more preferably a data transmission by the same.

In particular, the pen 1 just described is shaped so that the first portion 13 of the casing 10 substantially contains only the writing element 20 of the pen 1, while the second portion 15 contains the electronic module 40, the battery 50 and contains or mechanically supports the force sensor 30. Consequently, when the first portion 13 and the second portion 15 of the casing 10 are separated, a writing element 20, for example an exhausted refill, can be replaced in an extremely simple way with no need for any specific expertise.

Furthermore, the electronic module 40 is designed so that the IMU 43 is in a position proximal to a second end 19 of the casing 10 and distal from the first end 11 of the casing 10, with respect to the main direction P of the pen 1, when the pen 1 is assembled. In other words, the movement sensor of the pen 1 is located at the second end 19 of the pen 1. Thanks to this arrangement of the IMU 43, the impact of measurement errors is substantially reduced. In fact, during writing, the pen 1 performs rotational, oscillatory and similar movements around the writing end 21, resting on the surface on which signs are written. The IMU 43 positioned near the second end of the casing 19—i.e., away from the writing end 21—will detect accelerations of greater intensity than those to which the writing end 21 is subjected while the pen 1 is being used. Consequently, the ratio between the measurements made by the IMU 43 and the measurement errors will be better than if the measurement was made near the writing end 21. This allows obtaining particularly reliable and effective data for the recognition and analysis of the tremor while the writing instrument is being used. More generally, this arrangement of the IMU 43 allows obtaining particularly reliable and effective data for the recognition and analysis of neurological pathologies or learning disorders.

Figure 3A:
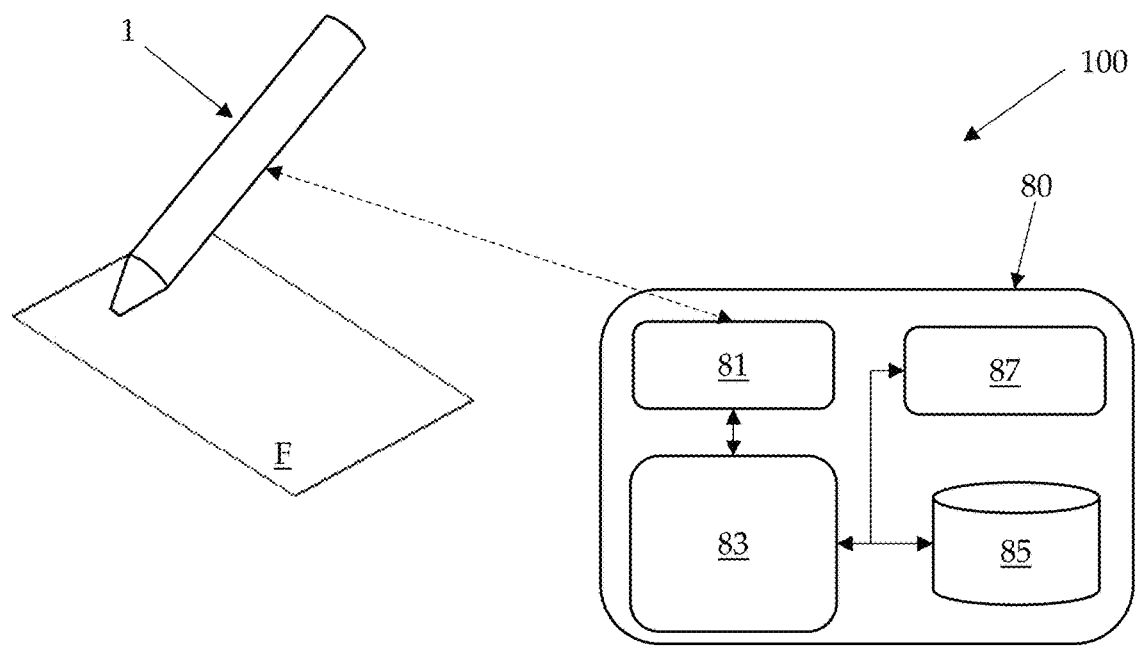
FIG. 3a illustrates a system for monitoring and analyzing handwriting according to an embodiment of the present invention.

The pen 1 may be part of a system 100 for analyzing handwriting schematically shown in FIG. 3a. The system 100 comprises the pen 1 and a processing device 80. The processing device 80 is configured to receive data from the pen 1 and process them, as described in greater detail below in order to analyze the handwriting of an individual using the pen 1. In particular, in the present description the expression 'analyze the handwriting of an individual using the pen 1' indicates the analysis of the information provided by the pen 1 in order to identify features to highlight one or more specific aspects—for example, a tremor—associated with the action of drawing a sign—for example, a written word or a drawing—performed by the individual holding the pen 1. To this end, the processing device 80 comprises a communication unit 81, configured to receive, but more preferably exchange, data from the BLE 44 of the pen 1 by means of a radio frequency connection, a control unit 83, configured to process the received data, a memory 85 configured to store received data, processing data and processing instructions, and a user interface 87 configured to provide information and receive instructions from a user. As will be evident to the person skilled in the art, the processing device 80 can be implemented through a single electronic device or a distributed physical and/or virtual network of electronic devices. For example, the processing device 80 may comprise processing and/or storage resources provided by one or more data centres and/or one or more of cloud computing and edge computing resources.

Figure 3B:
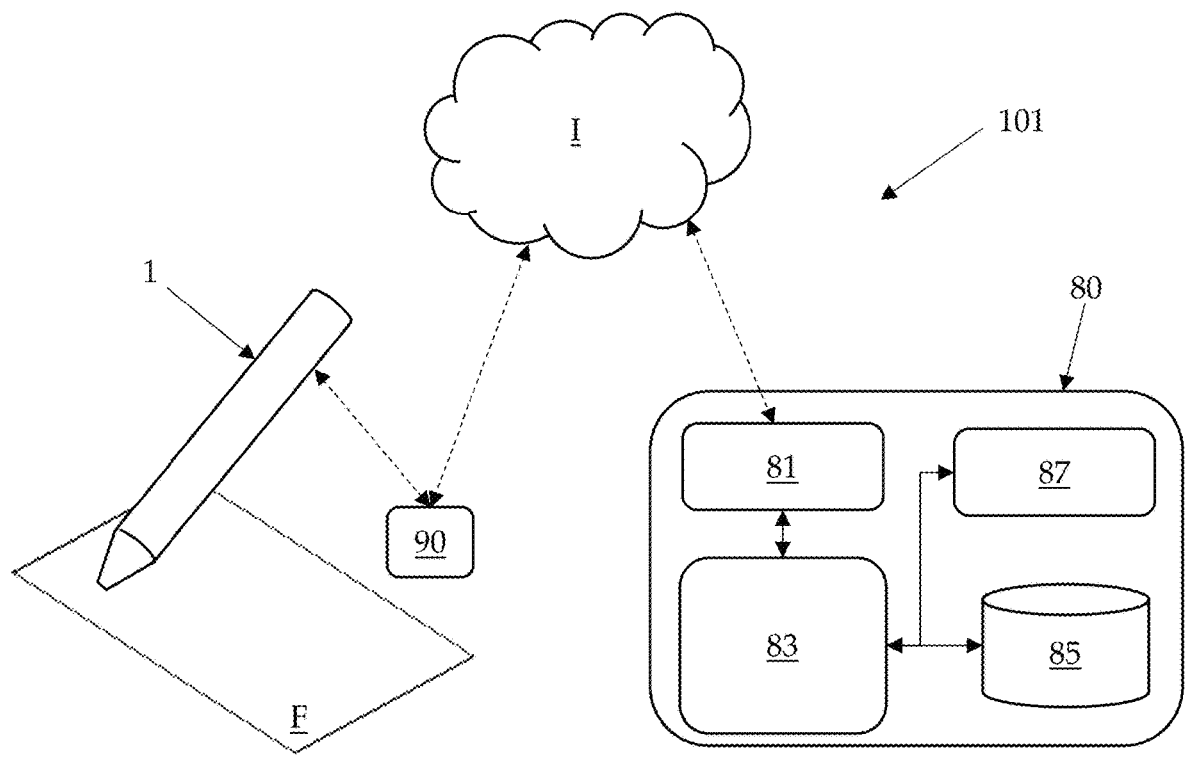
FIG. 3b illustrates a system for monitoring and analyzing handwriting according to a different embodiment of the present invention.

In an alternative embodiment, schematically shown in FIG. 3b, the system 101 entails that the pen 1 is connected and transfers data to an intermediate device 90, for example a smartphone, a modem, a switch, a console, etc. The intermediate device is in turn configured to establish a connection through a telecommunications network I (wired and/or wireless and/or internet) and transmits the data provided by the pen 1 to the processing device 80.

Figure 4:
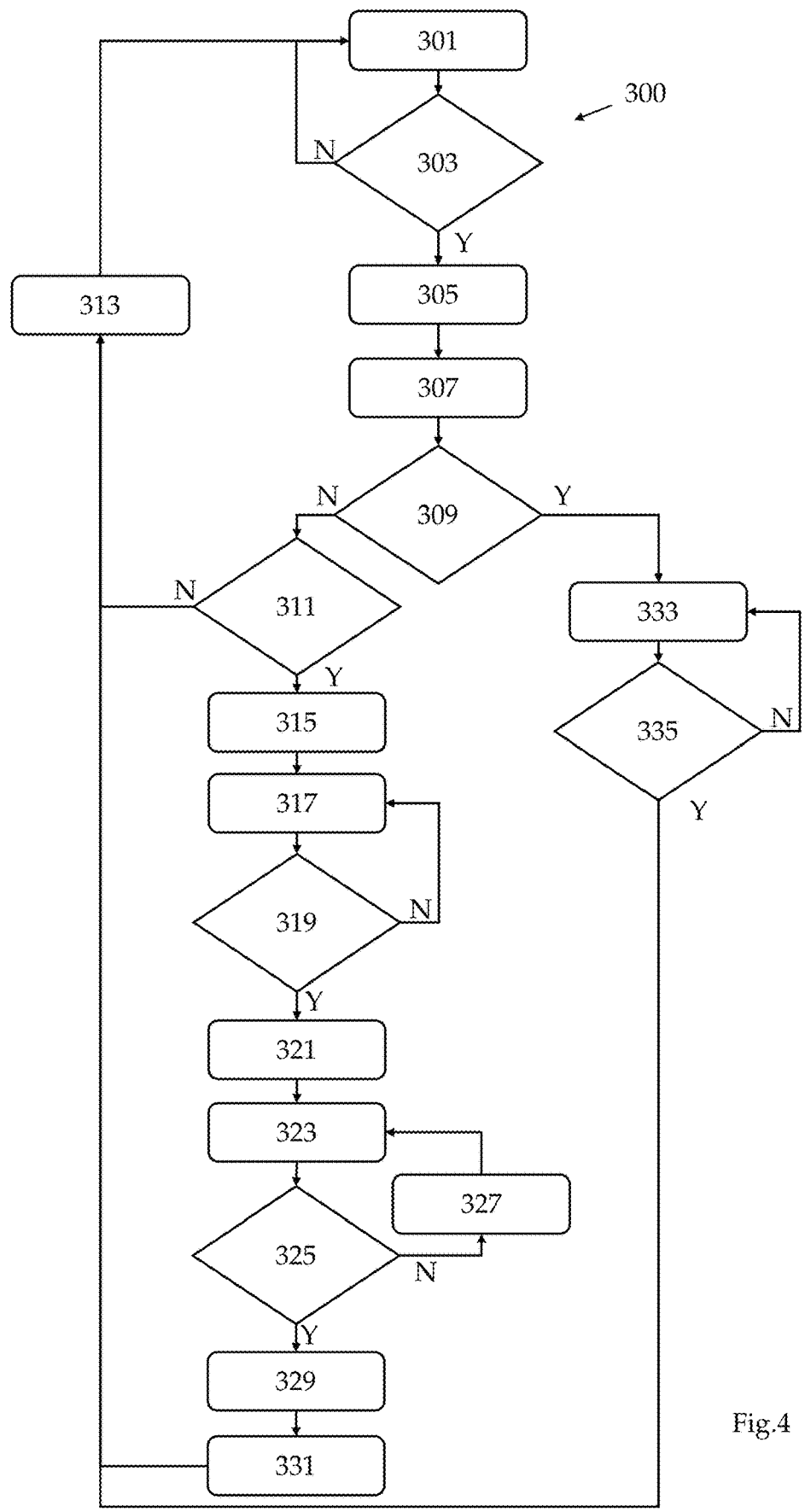
FIG. 4 is a flowchart illustrating a procedure for data acquisition and transmission by the writing instrument of FIGS. 1a and 1b.

In one embodiment, the control unit 41 of the pen 1 is configured to implement a data acquisition and transmission procedure 300 described below in relation to the flowchart of FIG. 4.

The procedure 300 comprises monitoring the movement measures $m_M$ provided by the IMU 43 (block 301). For example, the movement measures provided by the IMU 43 comprise three linear acceleration measures along reference axes x, y and z—where the axis z is preferably aligned to the main direction P of the pen 1 and oriented towards the second end 19 of the casing 10—and three measures of angular velocity referred to the same reference axes x, y and z. In other words, the movement measures $m_M$ provided by the IMU 43 correspond to a vector comprising three linear acceleration values and three angular velocity values as a function of time.

The movement measures $m_M$ are analyzed to detect an initial time instant to in which the movement measures exceed a first threshold value $th_1$ (decision block 303). In particular, the first threshold value $th_1$ is indicative of a passage from a stationary condition of the pen 1 to a movement condition thereof. In other words, the movement measures that exceed the first threshold value $th_1$ are considered as writing measures, indicative of an amplitude of movement compatible with a writing operation or, more generally, with tracing a sign. In the preferred embodiment, the first threshold value $th_1$ is a vector comprising three linear acceleration values and three threshold angular velocity values and the exceeding of one of such linear acceleration values and threshold angular velocity values by one of the corresponding values of the movement measures $m_M$ is considered as exceeding the first threshold value $th_1$. Preferably, the first threshold value $th_1$ is considered as exceeded when it is exceeded by one of the movement measures $m_M$ for a minimum time interval. For example, if the IMU 43 is implemented by an LSM6DSM module, the verification that the first threshold value $th_1$ has been exceeded can be performed by means of the wake-up function of this module.

If movement measures $m_M$ greater than the first threshold value $th_1$ are not detected (output branch N of block 303), it is envisaged continuing monitoring the movement measures $m_M$—in other words, the procedure 300 is repeated from the described step in relation to block 301.

Otherwise, when the detected movement measures $m_M$ are greater than the first threshold value $th_1$ (output branch Y of block 303), the unit BLE 44 is activated in order to allow establishing a communication channel with the processing device 80 within connection time period $T_{Max}$, i.e. a time interval included between the initial time instant to and a time limit instant $t_{Max}$ (i.e., $T_{Max}=t_{Max}-t_0$)—directed or through the additional device 90 and the communication network I—(block 305).

The movement measures $m_M$ are monitored to count a number of movement measures $m_M$ greater than the first threshold value $t_{h1}$ within a counting time interval $\Delta tC$ included between an intermediate time instant tI and the time limit instant $t_{Max}$ (i.e., $\Delta tC=tMax-tI$, with tI>t0) (block 307).

It is then verified whether a communication channel has been established between the unit BLE and the processing device 80 within the connection time period $T_{Max}$ (decision block 309).

If a communication channel is not established between the unit BLE and the processing device 80 within the connection time period $T_{Max}$ (output branch N of block 309), it is envisaged verifying whether the number of measures of $m_M$ greater than the first threshold value $th_1$ counted in the counting time interaction $\Delta t_C$ exceeds a second threshold value $th_2$—i.e., a predetermined number N of counts (decision block 311). In particular, the second threshold value $th_2$ identifies an interaction between pen 1 and monitored individual useful to be stored, which is indicative with a high probability of a use of the pen 1 by an individual (not shown) to write or, more in general, to draw a sign on a support F (for example, a sheet of paper or cardboard).

If a number of movement measures $m_M$ greater than the second threshold value $th_2$ is not detected within the counting time interval $\Delta t_C$ (output branch N of block 311), it is envisaged deactivating the unit BLE 44 (block 313) at the end of the connection time period $T_{Max}$ and resuming monitoring the movement measures $m_M$—in other words, the procedure 300 is repeated from the step described in relation to block 301.

Conversely, if a number of movement measures $m_M$ greater than the second threshold value $th_2$ is detected within the counting time interval $\Delta t_C$, but a communication channel has not been established between the unit BLE and the processing device 80 within the connection time period $T_{Max}$ (output branch Y of block 309), it is envisaged deactivating the unit BLE 44 (block 315) and storing the movement measures $m_M$ provided by the movement sensor 43 and the force measures $m_P$ provided by the force sensor 30 in the memory 42 of the electronic module 40 (block 317). For example, in case it is wished to identify tremors in handwriting, the measures of movement $m_M$ and pressure $m_P$ are sampled with a frequency equal to, or greater than, 30 Hz preferably equal to, or greater than, 50 Hz, so that the data acquired contain useful information about the tremor—as the highest frequency associated to tremor is essentially 25 Hz. Preferably, the movement measures $m_M$ and the force measures $m_P$ are stored together with an indication of the time instant, for example a timestamp—in which these measures are acquired.

The movement measures $m_M$ provided by the movement sensor 43 are monitored to identify a cancellation of one or more, preferably all, the movement measures $m_M$ provided by the movement sensor 43 (decision block 319). In other words, it is verified when one or more of the movement measures $m_M$ are equal to zero—or equal to or less than the threshold value $th_1$—, an event indicative of the termination or stop of a writing operation by the individual being examined.

In the negative case (output branch N of block 319), it is envisaged to continue storing the movement measures $m_M$ provided by the movement sensor 43 and the force measures $m_P$ provided by the force sensor 30 by repeating the procedure 300 from the previous block 317.

If a cancellation of one or more, preferably all, of the movement measures $m_M$ is detected (output branch Y of block 319), it is envisaged stopping the storage of movement measures $m_M$ provided by the movement sensor 43 and the force measures $m_P$ provided by the force sensor 30 (block 321) and reactivating the unit BLE 44 for a new communication time period $T_{Max}$, in order to make the movement measures $m_M$ and the force measures $m_P$ stored in the memory unit 42 available to the processing device 80 (block 323).

Next, the activity of the unit BLE 44 is monitored to verify the presence of a communication channel (wireless) between the unit BLE 44 and the processing device 80 within the communication time period $T_{Max}$ (decision block 325).

If a communication channel is not established between the unit BLE 44 and the processing device 80 (output branch N of block 325), the unit BLE 44 is switched off again for a waiting period t (block 327) before it is reactivated to allow a communication channel to be established with the processing device 80 by repeating the procedure 300 from what is described in relation to block 323.

When the communication channel is established between the unit BLE 44 and the processing device 80 (output branch Y of block 325), the transmission of the movement measures $m_M$ and of the force measures $m_P$ stored in the memory unit 42 to the processing device 80 is envisaged (block 329). At the end of the transmission, it is preferably envisaged carrying out a formatting—high level or low level—of the memory unit 42 (block 331). Subsequently, the procedure 300 continues as described above in relation to block 313.

If the communication channel between the unit BLE 44 and the processing device 80 is established within the connection time period $T_{Max}$ (output branch Y of block 309), it is envisaged transmitting directly to the remote device 80 the movement measures $m_M$ provided by the movement sensor 43 and the force measures $m_P$ provided by the force sensor 30 (block 333). In other words, the unit BLE 44 makes the movement measures $m_M$ provided by the movement sensor 43 and the force measures $m_P$ provided by the force sensor 30 available to the processing device 80, as a data streaming. Also in this case, preferably, the measures of movement $m_M$ and pressure $m_P$ are sampled before transmission with a frequency equal to, or greater than, 30 Hz, even more preferably equal to, or greater than, 50 Hz, in order to recognise tremors in handwriting. Preferably, the movement measures $m_M$ and the force measures $m_P$ are made available together with the timestamp, indicative of the time instant in which these measures are acquired.

Subsequently, it is envisaged monitoring the communication channel in order to identify a stop thereof, in particular, by the processing device 80 (decision block 335). If a stop of the communication channel is not detected (output branch N of block 335), it is envisaged continuing the transmission of the movement measures $m_M$ and of the force measures $m_P$ substantially in real time as described in relation to the previous block 333.

Otherwise, if a stop of the communication channel is detected (output branch Y of block 335), it is envisaged deactivating the unit BLE 44 by repeating the procedure 300 starting from what is described with reference to block 313.

Thanks to the procedure 300, the pen 1 is able to provide a large amount of data relating to the handwriting of the individual being examined at the processing device 80, substantially whenever the pen 1 is used by the individual in possession of the pen 1, with no need for supervision by a specialized operator or an external computer in connection with the instrument via BLE. This allows to acquire data relating to the handwriting of the individual for long periods of time, thus allowing an accurate analysis of the handwriting of the individual being examined and/or to identify more accurately variations in the handwriting style of the individual being examined, for example indicative of neurodegenerative pathology.

In the embodiments of the present invention the processing device 80 is configured to perform a plurality of processing procedures on the data provided by the pen 1.

A first procedure 400 makes it possible to distinguish single continuous movements, indicated as strokes in the jargon, separated from movement stops performed by the individual being examined while writing or drawing. In particular, a stroke sk is defined as a set of measures of movement $m_M$ and pressure $m_P$ acquired in a time interval of strokes $\Delta t_s$ during which the force measure $m_P$ is not null preceded and followed by instants of time in which the force measure $m_P$ is null or below a lower limit value—in other words, the time interval of strokes zits is a time interval in which a force is exerted on the writing element 20 of the pen 1 having at least one component aligned to the main direction P and directed towards the writing end 21 of the writing element 20.

The procedure 400 (of which a flow diagram is shown in FIG. 5) initially envisages determining a static disturbance, or offset, on the force measure $m_P$ during writing (block 401). For example, the disturbance offset is defined as the mode of the median filter calculated on a predetermined number of samples of the force measure $m_P$, for example 50 samples, of an initial set of force measures nip provided by the force sensor 30—or similarly, the offset can be evaluated on a set of measures acquired during an offset time period.

This offset is then subtracted from the force measures nip provided by the force sensor 30 (block 403). In particular, it is possible to remove the offset from the same force measures $m_P$—i.e., from the samples mentioned above—used to determine the offset.

Subsequently, the force measures nip provided by the force sensor 30 are processed to remove slow variations, deviations due to measurement errors and random noise, also referred to collectively as the baseline (block 405)—comparable to a low frequency oscillation. In the example considered, the force measures received from the pen 1 and deprived of the offset are provided as input to an algorithm for estimating and removing the baseline and the noise which, preferably, uses the concept of sparsity. For example, the processing device implements an adapted version of the BEADS algorithm by Matlab® also described in Xiaoran Ning, Ivan W. Selesnick, Laurent Duval: "*Chromatogram baseline estimation and denoising using sparsity (BEADS)*", Chemometrics and Intelligent Laboratory Systems, December 2014.

The values of the force measures nip thus treated below a minimum threshold value—for example, determined in an instrument calibration step—are brought to zero (block 407).

The information provided by the force sensor 30 alone is therefore sufficient to reliably distinguish time instants in which the pen 1 is raised from the support F, corresponding to the periods with force measure $m_P$, and time instants in which signs are drawn with the pen 1 on the support F, corresponding to periods with non-null force measure $m_P$.

Each set of non-null force measures nip that are consecutive over time is identified as a corresponding stroke sk (as shown in the example of FIG. 6) performed by the individual being examined (block 409).

Preferably, it is envisaged associating together the force and movement measures acquired during the execution of the same stroke sk stored in the memory 85 of the processing device 80 (block 411). In other words, the measurements acquired by the sensors 30 and 43 provided by the pen 1 grouped based on the strokes sk identified in the memory 85 of the processing device 80.

Otherwise, a second procedure 500 allows estimating a tilt of the pen 1 during the use thereof.

The second procedure 500 (as shown in the flow chart of FIG. 7) envisages verifying whether the pen is in a condition of static or semi-static use, or in a condition of dynamic use (decision block 501). For example, the condition of use is discriminated on the basis of the values of the movement measures $m_M$ provided by the IMU 43, in particular, the pen 1 is considered in a condition of static or semi-static use when one or more values of the movement measures $m_M$ varies with a frequency lower than a threshold frequency value, otherwise the pen 1 is considered in a condition of dynamic use when one or more values of the movement measures $m_M$ vary with a frequency higher than the threshold frequency value.

If a condition of dynamic use is identified (output branch D of block 501), it is envisaged combining the linear acceleration and angular velocity measures provided by the IMU 43 to identify a variation rate, i.e. an angular velocity $\hat{\vartheta}$, as a function of the time of the tilt angle $\vartheta$ of the pen 1 with respect to the horizontal or the normal to the support on which handwriting is performed.

In particular, the procedure 500 envisages calculating a first tilt angular velocity $\hat{\vartheta}_g$ through the angular velocity measures contained in the movement measures $m_M$ provided by the IMU 43 (block 503)—in particular, by means of the angular velocity measures with respect to the axes x and y. Similarly, it is envisaged calculating a second tilt angular velocity $\hat{\vartheta}_a$ through the linear acceleration measures contained in the movement measures $m_M$ provided by the IMU 43 (block 505) and then determining the tilt angle $\hat{\vartheta}_a$ (block 507). Consequently, an adjusted tilt angular velocity $\hat{\vartheta}$ of the pen 1 is calculated according to the formula:

$$\hat{\vartheta}=k_1\hat{\vartheta}_g+k_2(\hat{\vartheta}_a-\vartheta), \quad (1)$$

where $k_1$ is a constant parameter comprised between 1.2 and 1.7, preferably equal to 1.5, and $k_2$ is a constant parameter comprised between 0.3 and 0.6, preferably equal to 0.4 (block 509).

Optionally, starting from the total tilt angular velocity $\hat{\vartheta}$ the value of the tilt angle $\vartheta$ is calculated as a function of time (block 511).

Finally, the total tilt angular velocity $\hat{\vartheta}$—and the values of the tilt angle $\vartheta$, if calculated—is stored in the memory 85 of the processing device 80 and is associated to the corresponding measures of movement $m_M$ and of pressure $m_P$ provided by the IMU 43 and by the force sensor 30 of the pen 1 (block 513). In particular, for a subsequent operation of recognition of indicators of neurological pathologies and/or writing analysis, the values of total tilt angular velocity $\hat{\vartheta}$ and of the tilt angle $\vartheta$ associated to non-null pressure measurements $m_P$ are particularly relevant.

Otherwise, if a condition of static or semi-static use is verified (output branch S of block 501), it is envisaged using the measurement of the accelerometer aligned to the axis z comprised in the movement measures $m_M$ in order to calculate the tilt angle of the pen 1 through the following formula:

$$\vartheta = \sin^{-1}\left(\frac{a_z}{g}\right), \quad (2)$$

where $a_z$ is the measure provided by the accelerometer aligned to the axis z and g is the acceleration of gravity (block 515).

Optionally, formula (2) can be replaced by the following linear approximation for small angles:

$$\vartheta \cong k \times \left(\frac{a_z}{g}\right), \quad (3)$$

with k=1.

A third procedure 600 performed by the processing device 80 allows to identify the symbols written by the individual under examination.

In detail, procedure 600 envisages implementing a neuronal network trained to recognise one or more symbols traced by the individual by means of the pen 1.

Initially, procedure 600 (as shown in the flowchart of FIG. 8) envisages collecting the measurements provided by the force sensor 30 and by the IMU 43 of the pen 1 in a plurality of time series x(t) of measurements to be analyzed (block 601). Preferably, each time series is defined as:

$$x(t)=[f(t),\partial(t)]' \in R^2, \quad (4)$$

Where $f(t)$ represents the trend as a function of the time of the pressure obtained from the force measures $m_P$ provided by the force sensor 30 of the pen 1 and $\partial(t)$ represents the trend as a function of the time of the tilt angle of the pen 1 obtained from the movement measures $m_M$ provided by the IMU 43.

For example, each time series x(t) corresponds to a stroke sk identified through the procedure 400 described above.

Each time series x(t) is provided as input to the neuronal network, preferably of the recursive type, which identifies it on the basis of a comparison with a plurality of previously acquired training sequences, a symbol sy corresponding to, or comprising, the stroke sk analyzed (block 603).

In one embodiment, the training envisages acquiring a plurality of training sequences $x_a(t)$ for each symbol to be recognised, by having this symbol written by a plurality of sample subjects. Preferably, each training sequence $x_a(t)$ has the same duration, for example equal to 1.2 s—i.e., it comprises 60 measurement samples with a sampling frequency at 50 Hz mentioned above, where it is envisaged applying a zero-padding strategy in order to reach 60 samples in case of training sequences with fewer samples. For example, the neural network implemented by the remote device 80 is based on what is described in K. Greff, R. K. Srivastava, J. Koutnik, B. R. Steunebrink and J. Schmidhuber: "*LSTM: A Search Space Odyssey*", IEEE Transactions on Neural Networks and Learning Systems, vol. 28, no. 10, pp. 2222-2232, October 2017 and similarly trained based on what is described in Akhundov, Adnan & Trautmann, Dietrich & Groh, Georg: "*Sequence Labeling: A Practical Approach*", 2018, arXiv: 1808.03926.

Finally, the result of the analysis of the neuronal network, i.e. an indication relating to the identified symbol sy and, preferably, a confidence value of such identification are stored in the memory 85 associated to the corresponding stroke sk (block 605).

Figure 9:
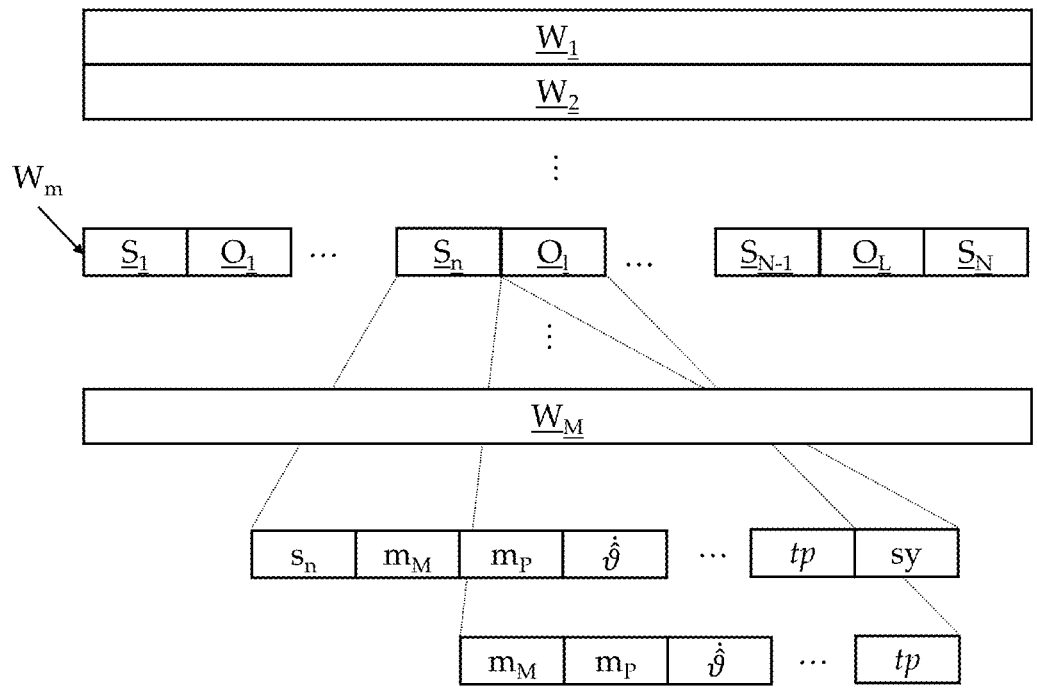
FIG. 9 is a basic diagram of an organization of the writing data detected and processed by the system of FIGS. 3a and 3b according to an embodiment of the present invention.

As will be evident to the person skilled in the art from what is indicated above, the processing device 80 can be configured to store the measurements provided by the pen 1 and the results of carrying out the procedures 400-600 described above in an organized manner. Advantageously, as schematically shown in FIG. 9, the data relating to the handwriting obtained—i.e., measured or processed—in relation to the same handwriting time period are identified as part of the same handwriting $W_m$. In addition, the movement measures $m_M$, the force measures MP, the timestamp associated to the measures, the tilt angular velocity $\hat{\vartheta}$—and the tilt angle $\vartheta$, if calculated —, the identified symbol sy—and the relative confidence value if calculated—relating to the same stroke s are grouped in a dataset of strokes S. Furthermore, at least in the case of a writing flow $W_m$ acquired through direct transmission, the writing flow $W_m$ comprise an "in-air" dataset O i.e. associated to an instant in which the individual moves the pen 1 away from the support F between one stroke s and the next. Also the in-air dataset O comprises movement measures $m_M$, whereas the force measures $m_F$ are null as the pen 1 is separated from the support F, the timestamp tp associated to the measures, the tilt angular velocity $\hat{\vartheta}$—and the tilt angle $\vartheta$, if calculated—relating to the same time period between consecutive strokes s. Thus, the memory will comprise a plurality of writing flows $W_{1-M}$ (with M as natural integer) indicative of different writing operations performed by the individual during corresponding periods of time. Each, writing flow $W_m$ (with m comprised between 1 and M) comprises a plurality of datasets of strokes $S_{1-N}$, whereby N is a natural integer corresponding to the number of strokes s identified during the writing flow $W_m$ interspersed with in-air datasets $O_{1-L}$, whereby L is a natural integer corresponding to the number of periods of time in which the force measure $m_F$ is nullified between one stroke and the consecutive one.

Furthermore, the processing device 80 is configured to perform a procedure 700 for analyzing handwriting of the individual, in order to identify variations in the handwriting ability of the individual being examined, for example, an undermining in the handwriting ability due to the onset of a neurodegenerative pathology.

The procedure 700 envisages comparing one or more of the data stored in the datasets of strokes $S_n$ of the different writing flows $W_m$ stored by the processing device 80 and providing indications on variations while carrying out the handwriting by the individual being examined.

Figure 10:
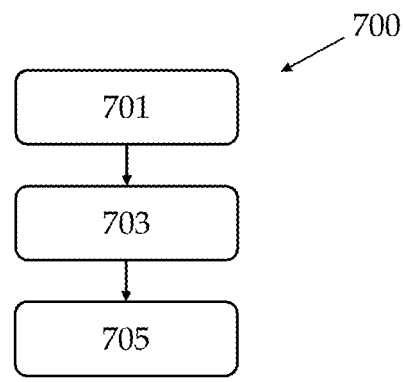
FIG. 10 is a flowchart illustrating a procedure for analyzing handwriting based on the collected information performed by the processing device of the system of FIGS. 3a and 3b according to an embodiment of the present invention.

In one embodiment, the procedure 700 (as shown in the flow diagram of FIG. 10) envisages identifying similar strokes sk belonging to a plurality of different writing flows $W_m$ therefore acquired at different time instants (block 701). For example, the procedure 700 envisages identifying strokes sk belonging to different writing flows $W_m$ associated to the same symbol identified through the procedure 600.

Subsequently, it is envisaged analyzing the datasets of strokes Sn corresponding to this plurality of identified strokes sk in order to identify significant variations between successive writing flows Wm over time (block 703). In other words, variations are identified in the writing style of the same symbol by the individual being examined as the time has lapsed. For example, algorithms are applied which envisage determining correlation, variance and/or other statistical information by comparison of the datasets of strokes Sn capable of highlighting a change in the writing ability of the individual. In addition or alternatively, a neuronal network is envisaged that is trained to identify progressive variations in the sequence of analyzed datasets of strokes Sn.

Finally, a report indicating the type of identified variation is generated, which is provided to a user of the processing device 80 through the user interface 87 (block 705).

However, it is clear that the above examples must not be interpreted in a limiting sense and the invention thus conceived is susceptible of numerous modifications and variations.

For example, the sensors may have a different positioning within the pen. In particular, although the movement sensor is preferably housed in a position having a shorter distance from the second end of the casing with respect to a distance from the first end thereof, nothing prevents the movement sensor from being located in other embodiments near the writing end of the writing element, the refill in the example considered above.

For example, in an alternative embodiment—shown in FIGS. 11a, 11b, 12 and 13, where numerical references similar to those used indicate elements similar to those described above and the description of which is not repeated for brevity's sake—, the pen 1A has a structure such as to allow to expose and retract the writing end 21 of the writing element 20 and, at the same time, to activate and deactivate, respectively, the electronic module 40.

The casing 10 of the pen 1A comprises a third portion 14 interposed between the first portion 13 and the second portion 15. In particular, the third portion 14 comprises a first element 141 and a second element 143, which are shaped in such a way as to be slidingly fastened to each other.

In detail (as can be better observed in FIGS. 11b, 12 and 13), the first element 141 has an elongated cylindrical shape which comprises a through hole 1411, preferably coaxial to the first element 141 and which extends along the main direction P when the pen 1A is assembled. The first element 141 can be fastened to the first portion 13, for example, a first end 1412 of the first element 141 comprises a coupling element—a thread—configured to be coupled to a corresponding coupling element—a corresponding thread—formed at the aperture 17 of the first portion of the casing 10.

A second end 1413 of the first element 141 is shaped to surround the end of the second portion 15 of the casing which comprises the aperture 18. In particular, the second end 1413 comprises a circular shoulder configured to receive an edge of the aperture 18 of the second portion 15 of the casing 10. An electrical contact 1415, for example an annular sheet made of aluminium or copper, is arranged at the shoulder.

A pair of guide grooves 1416, preferably helical, is formed in an internal wall of the first element that delimits the through hole 1411. Each of the guide grooves 1416 is adapted to slidingly receive a respective pin 1431 projecting from the second element 143 in a radial direction with respect to the main length direction of the second element 143 which corresponds to the main length direction P when the pen 1A is assembled.

In particular, the second element 143 of the third portion 14 of the casing 10 has a cylindrical shape having a cross section lower than the cross section of the through hole 1411 of the first element 141 of the third portion 14, so as to be insertable inside the same, with the pins 1431 inserted into the guide grooves 1416.

Furthermore, the second element 143 of the third portion 14 of the casing 10 comprises a through hole 1432, preferably coaxial to the second element 143 and which extends along the main direction P when the pen 1A is assembled. A first end 1433 of the second element 143 comprises a shoulder configured to receive an end of a helical compression spring 131 housed in a through hole 132 of the first portion 13 when the pen 1A is assembled. Otherwise, a second end 1435 of the second element 1435 comprises a coupling element—a thread—configured to be coupled to a corresponding coupling element—a corresponding thread—formed at the aperture 18 of the second portion of the casing 10.

When the pen 1A is assembled, the through hole 1411 of the first element 141, the through hole 1432 of the second element 143 of the third portion 14 of the casing 10, and the through hole 132 of the first portion 13 are coaxial with each other and substantially aligned to the main length direction P of the pen 1A. The through hole 1432 of the second element 143 of the third portion 14 and the through hole 132 of the first portion 13 define a housing of the writing element 20.

In particular, the through hole 1432 of the second element 143 of the third portion 14 has a cross section adapted to receive substantially a body 22 of the writing element 20 to size and comprises an enlarged portion at the second end of 1435 of the second element 143 configured to receive a terminal end 23 of the writing element 20—opposite the writing end 21—, so as to hold the latter in position and prevent the writing element 20 from coming off the pen 1A during the use thereof.

Figure 13:
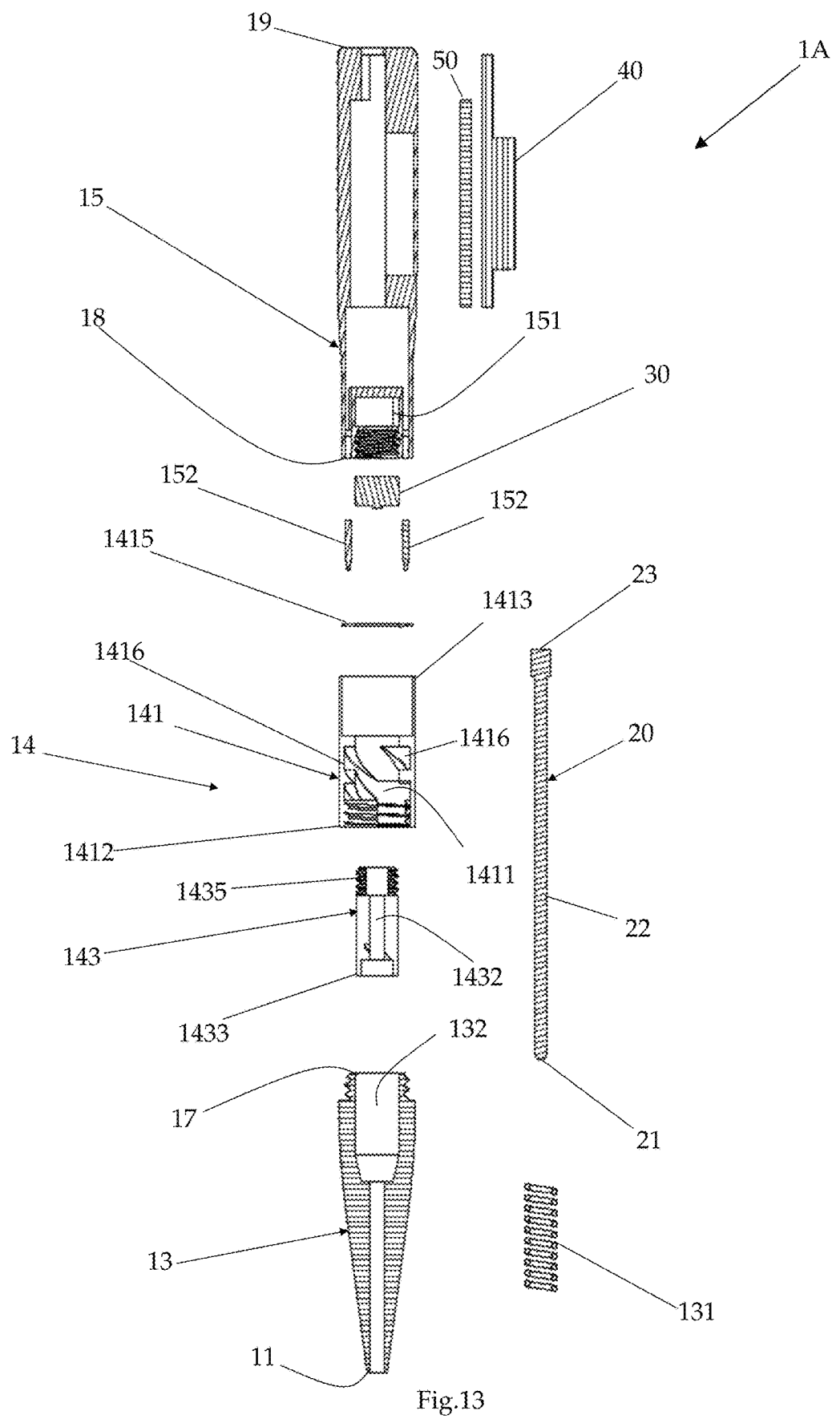
FIG. 13 is a sectional side view of the exploded view of FIG. 12 along the section plane 7E.

The second portion 15 of the casing 10 comprises, near the aperture 18, a housing 151 for the force sensor 30—preferably a load cell. In the example of FIGS. 11b and 13, the housing 151 comprises an aperture, preferably coaxial to the main length direction P when the pen 1A is assembled, configured to allow direct contact between the force sensor 30 and the terminal end 22 of the writing element 20 when the pen 1A is assembled.

Figure 11A:
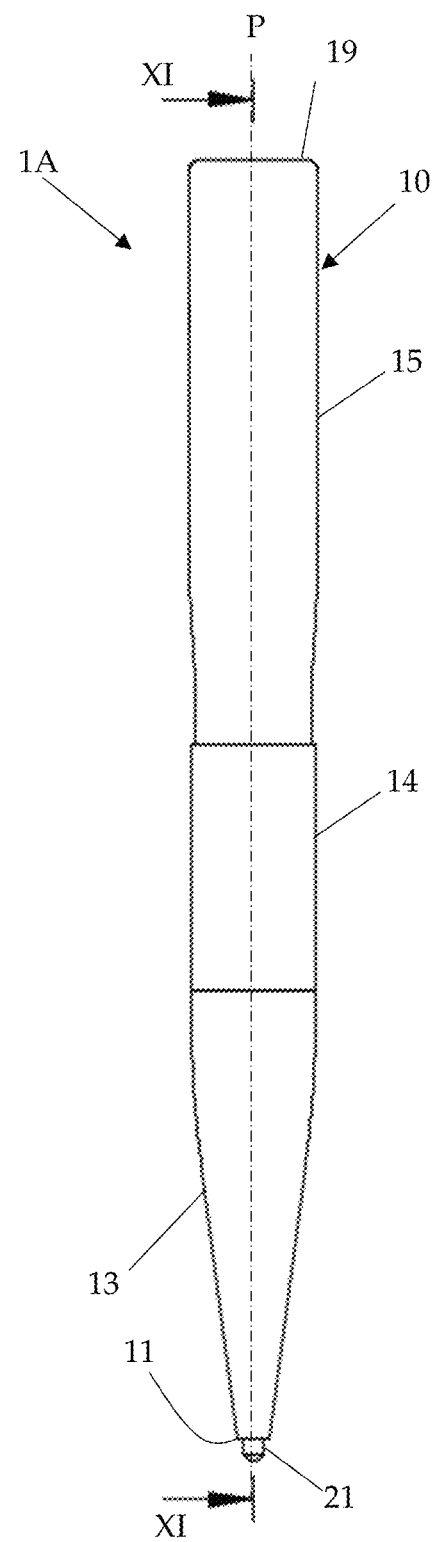
FIG. 11a is a side view of a writing instrument according to an alternative embodiment of the present invention.
Figure 11B:
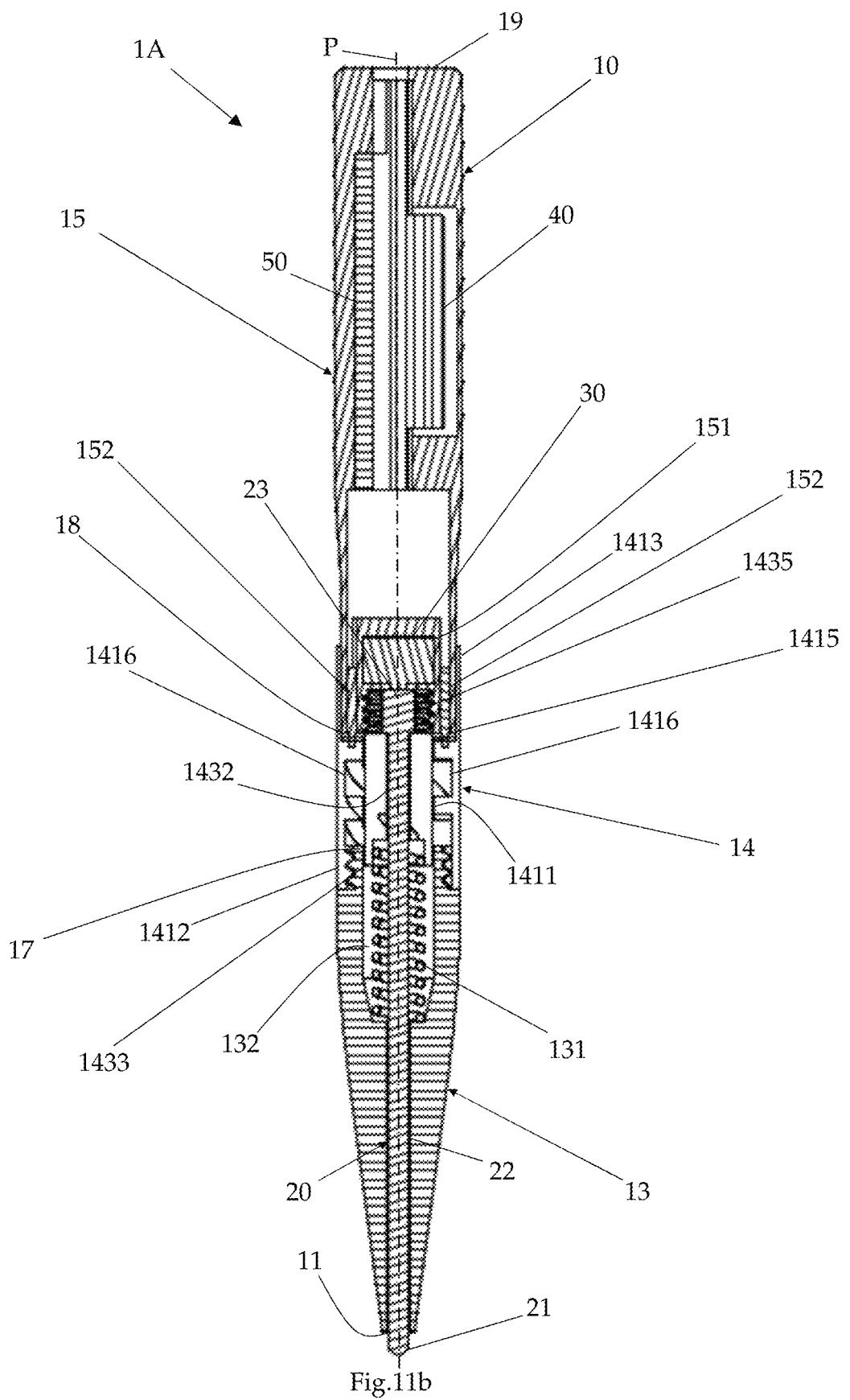
FIG. 11b is a sectional side view of the writing instrument of FIG. 11a along the section line XI-XI.
Figure 12:
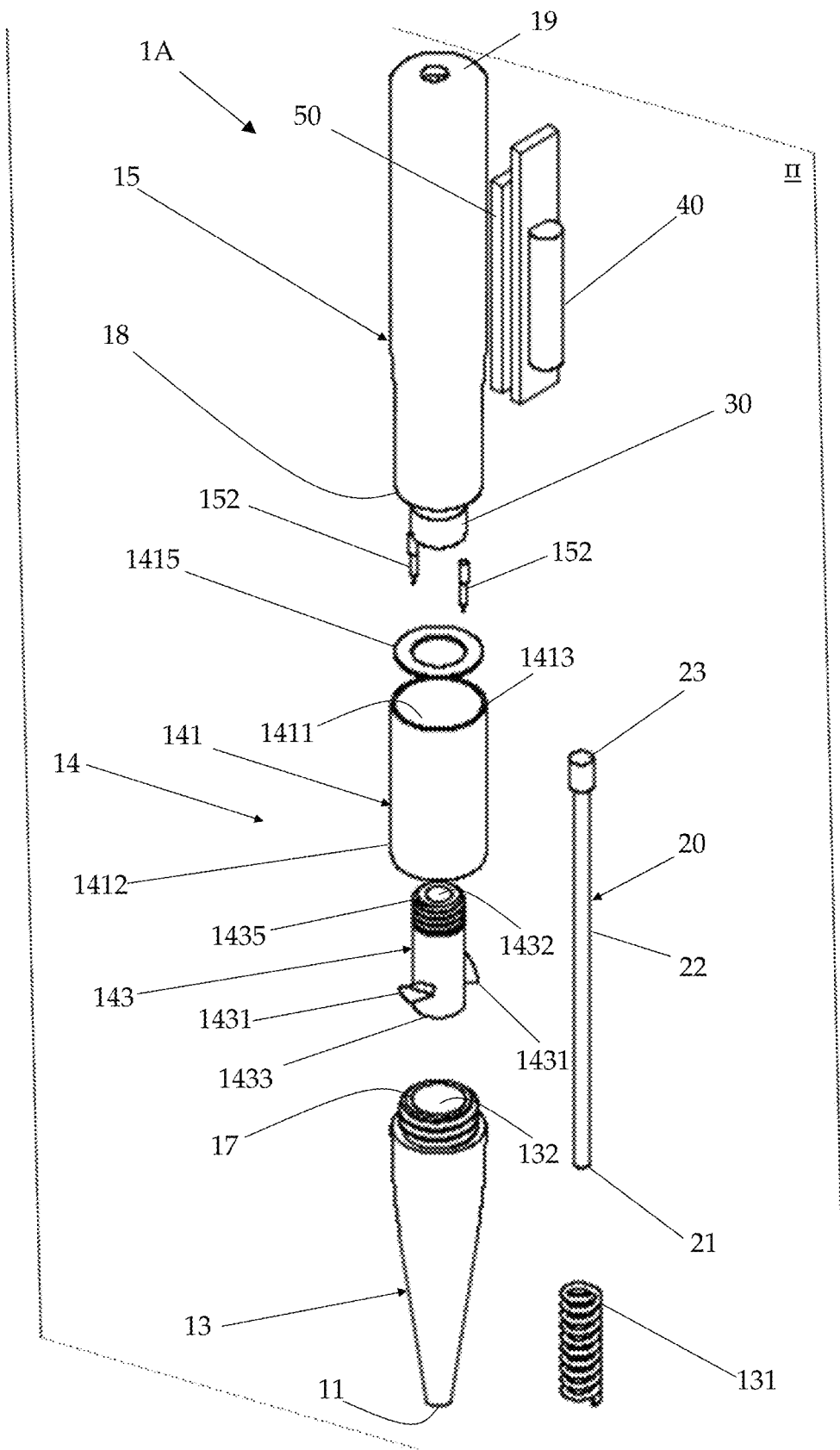
FIG. 12 is an exploded axonometric view of the writing instrument of FIGS. 11a and 11b.

Furthermore, near the aperture 18, the second portion 15 of the casing 10 comprises at least one pair of housings for the same number of electrical contacts, pogo pin 152 in the example of FIGS. 11b, 12 and 13. These pogo pins 152 are arranged in the respective housings so as to have one (retractable) end exposed at the aperture 18.

Finally, although not shown in FIGS. 11b, 12 and 13 for simplicity's sake, the sensor 30 and the pogo pins 152 comprise respective electrical connections to the electronic module 40 or to the battery 50. In detail, the sensor 30 is connected at least to the electronic module 40, while the pogo pins 152 define a connection circuit between the battery 50 and the electronic module 40 through which electrical energy is selectively supplied from the battery to the electronic module 40 as described below.

When the pen 1A is assembled, the first element 141 of the third portion 14 is fastened to the first portion 13 of the casing 10. Otherwise, the second element 143 of the third portion 14 is fastened to the second portion 15 of the casing 10. Finally, the first element 141 and the second element 143 of the third part 14 of the casing 10 are slidingly coupled together, by means of the coupling between the grooves 1416 and pins 1431.

In particular, pins 1431 are free to slide in the grooves 1416 between a first stop position in which the writing end 21 of the writing element 20 is contained within the first portion 13 of the casing 10 and a second stop position in which the writing end 21 of the writing element 20 is exposed through the first end 11 in the first portion 13 of the casing 10 (as shown in FIGS. 11a and 11b).

In the first stop position the apertures 17 and 18 of the first portion 13 and of the second portion 15 of the casing are at a maximum distance from each other along the main length direction P, whereas in the second stop position the apertures 17 and 18 of the first portion 13 and of the second portion 15 of the casing are at a maximum distance from each other along the main length direction P.

Furthermore, when the pins 1431 are in the first stop position of the grooves 1416, the pogo pins 152 exposed at the aperture 18 of the second portion 15 of the casing 10 are spaced from the electrical contact 1415 arranged in the shoulder 1414 formed in the end of the first element 141 of the third portion 14 of the casing 10 facing the aperture 18. Consequently, when the pins 1431 are in the first stop position of the grooves 1416, the electronic module 40 is not powered since the connection circuit between the latter and the battery 50 is open. Conversely, when the pins 1431 are in the second stop position of the grooves 1416, the pogo pins 152 come into contact with the electrical contact 1415. Consequently, when the pins 1431 are in the second stop position of the grooves 1416, the electronic module 40 is powered since the connection circuit between the latter and the battery 50 is open.

Consequently, the same reciprocal rotation action between the first element 141 and the second element 143 of the third portion 14 which causes the pins 1431 to slide from the first stop position to the second stop position has the effect of both exposing the writing end 21 of the writing element 20 and of starting the supply of electrical energy to the electronic module 40. Conversely, the same reciprocal rotation action between the first element 141 and the second element 143 of the third opposing portion 14 which causes the pins 1431 to slide from the second stop position to the first stop position has the effect of both hiding the writing end 21 of the writing element 20 and of stopping the supply of electrical energy to the electronic module 40. In other words, a user who imparts a reciprocal rotation between the first element 141 and the second element 143 of the third portion 14 for extracting the writing end 21 of the writing element 20 will simultaneously activate the electronic module 40. Vice versa, the user who imparts a reciprocal rotation between the first element 141 and the second element 143 of the third portion 14 for retracting the writing end 21 of the writing element 20 will simultaneously deactivate the electronic module 40.

Although the embodiments described above refer to a ballpoint pen, it is evident that in other embodiments (not shown) the writing instrument may be different, such as an infinite pencil, a pop-a-point type pencil, a marker, etc.

Furthermore, alternative embodiments (not shown), may provide a thrust element—for example a spring—adapted to push the writing element—the refill or a pencil core—outwards along the main direction of the writing instrument. In this case, the control unit on board the writing instrument or the processing device are configured to compensate for the force component exerted by said thrust element.

Nothing prevents from using an element other than an IMU to cause the movement of the writing instrument. For example, the movement sensor can comprise, for example, one or more linear acceleration sensors, angular velocity sensors, gyroscopes, a magnetometer, etc., advantageously arranged near the end of the casing opposite the end from which the writing element protrudes. In general, the movement sensor of a writing instrument according to the present invention provides an indication relating to the movement of the writing instrument in a three-dimensional space.

Similarly, the pressure applied by the individual while writing can be detected by a force sensor other than a load cell, such as a resistive sensor, a capacitive sensor or another similar sensor.

Again, nothing prevents the system from comprising several writing instruments according to the present invention, configured to be connected and transmit data to the same processing device. The processing device is in turn configured to separately process the writing flows provided by each writing instrument.

Additionally or alternatively, the processing device can be configured to use the measurements provided by the associated writing instruments to generate new training datasets for the neuronal networks in use.

Furthermore, nothing prevents the processing device from implementing one or more updating or adjustment procedures that provide for the transmission of configuration instructions to the writing instrument to modify its operation.

As will be evident to the person skilled in the art, one or more steps of the procedure 300 described above can be performed in parallel with each other—such as the steps relating to blocks 315-319, the steps relating to blocks 321-327, as well as the steps relating to blocks 329 and 331—or with a different order from the one presented above. Similarly, one or more optional steps can be added or removed from one or more of the procedures described above.

Furthermore, it will be evident that the activation of the transmission channel and/or its suspension can be controlled by the processing device and/or by the control unit of the pen.

According to an alternative embodiment (not shown) the control unit of the pen is configured to implement an alternative measurement acquisition procedure, which envisages:
  monitoring the measurements provided by the movement sensor, and
  activating the communication unit when a movement measure greater than the first transmission threshold value is detected;
  in series or in parallel, storing the measurements provided by the plurality of sensors, when a number greater than the second threshold value of movement measures exceeding the first threshold value is detected, and
  wherein the communication unit is configured for:
  transmitting at least part of the stored measurements when a connection is established with the remote device.

In another embodiment, the control unit is configured for:
  monitoring the measurements provided by the movement sensor, and
  activating the communication unit when a movement measure greater than a threshold value is detected;
  counting a number of movement measures that exceed said first threshold value within a counting time interval, preferably comprised between a time instant in which the communication unit is activated and a maximum time instant, and
  when a connection to the remote device is established before the connection time reaches the maximum time instant, the communication unit is configured to transmit the measurements provided by the plurality of sensors if the number of movement measures counted within said counting time interval exceeds the second threshold value.

Additionally or alternatively, the transmission of the data stored in the memory unit can be performed only once a predetermined condition has been identified.

In another embodiment, particularly suited for using the pen for the execution of the test in a controlled environment, the remote device is configured to transmit a memorization start command when it detects that the communication unit of the pen is active.

In detail, the pen control unit is configured to implement an alternative measurement acquisition procedure, which envisages:
  monitoring the measurements provided by the movement sensor,
  activating the communication unit when a movement measure greater than the first transmission threshold value is detected;
  when a connection is established between the communication unit and the remote device, receiving a memorization start command, and
  storing the measurements provided by the plurality of sensors in the memory unit.

In addition, it is envisaged the remote device to transmit a memorization stop command, in response to the reception of which, the control unit of the pen is configured to:
  stopping the storage of the measurements provided by the plurality of sensors in the memory unit.

Optionally, the communication unit can be switched off until discontinuation in the use of the pen is detected—for example when the movement measure is null or less than the first threshold value for at least a predetermined period of time. Alternatively, the communication unit can be switched off and back on periodically.

Preferably, the control unit of the pen is configured to transmit at least part of the stored measurements when a connection is established with the remote device, after:
  having received a memorization stop command from the remote unit,
  having received a data transmission command from the remote unit, or
  a discontinuation in the use of the pen has been detected In one embodiment, the remote device is configured to transmit the memorization start command only when a connection with a speed—for example in terms of bitrate bit/s—less than a threshold value is detected, in order to ensure a continuity of the acquired data and to minimize a possibility of losing information during transmission. Similarly, the acquisition of the data stored in the memory unit by the remote device can be performed once an adequate connection velocity to ensure a correct transmission of the information is detected.

For example, in one embodiment, the measurements stored in the memory unit are made available to the remote processor only when it is detected that the pen is connected to a power source for recharging the battery. Again, nothing prevents the processing device from being configured to transmit a request to make available any data stored in the memory unit of the pen when a communication channel is established.

In addition or alternatively, nothing prevents—in an alternative procedure (not shown)—from providing that the pen can suspend or stop the communication channel with the processing device in response to the detection of a predetermined event. For example, the control unit of the pen may be configured to deactivate the unit BLE when a cancellation of one or more, preferably all, of the movement measures for a predetermined period of inactivity is detected.

In alternative embodiments, the algorithm for eliminating the baseline used in procedure 400 can be defined by adapting the teachings contained in Barkauskas, Donald A, and David M Rocke. "*A general-purpose baseline estimation algorithm for spectroscopic data*" Analytica chimica acta, 2010, vol. 657,2 pages 191-7, in Vincent Mazet "*Background correction*" (https://www.mathworkscom/mat/abcentral/fileexchange/27429-background-correction), MATLAB Central File Exchange, Retrieved Mar. 26, 2020, or in Zhang, Zhimin & Chen, Shan & Liang, Yi-Zeng; "*Baseline correction using adaptive iteratively reweighted penalized least squares*" The Analyst, 2010, Vol. 135, pages 1138-46.

Again, nothing prevents from configuring the procedure 600 to analyze time series consisting of a set of consecutive strokes and, possibly, on-air periods, rather than a single stroke. In particular, time series can correspond to a symbol or an entire word.

It will be apparent to the person skilled in the art that a single, or a combination of two or more, of the procedures 400-700 presented above form a method for analyzing handwriting of an individual being examined. In addition, one or more steps of the same procedure or of different procedures can be performed in parallel with each other or with a different order from the one presented above. Similarly, one or more optional steps can be added or removed from one or more of the procedures described above.

Again, the system 1 can be configured to perform a procedure for analyzing writing flows W in which the stored data are analyzed as a whole to recognise a symptom of a neurodegenerative pathology regardless of the specific symbol or stroke written. For example, the analysis procedure is configured to extract indicators of tremor—for example frequency, amplitude, entropy, etc. of handwriting—and monitor them over time, allowing to identify the onset of a tremor, even regardless of the identification of micrographic phenomena in the writing flows produced by the individual being examined by means of the writing instrument.

Naturally, all the details can be replaced with other technically-equivalent elements.

For example, although in the above description reference has always been made to handwriting, nothing prevents from using the pen and the system according to the embodiments of the present invention for monitoring and analyzing a drawing operation performed by the individual by means of the writing instrument.

Again, although in the description reference has been mainly made to neuronal pathologies, nothing prevents from analyzing the time trend of pressure and of the graphic line in order to carry out the early diagnosis of dysgraphia in children, to provide graphology information, and the like.

Furthermore, although the writing instrument and the system according to the present invention are particularly suitable for monitoring and for analyzing handwriting that is transparent for the user, nothing prevents the use thereof for the execution of controlled tests.

In addition, nothing prohibits using the writing instrument and/or the entire system according to the embodiments of the present invention as a user interface for performing interactive tasks not necessarily related to the writing analysis, such as for example carrying out so-called exergames or serious games that comprise writing and/or drawing tasks.

In conclusion, the materials used, as well as the contingent shapes and dimensions of the aforementioned devices, apparatuses and terminals, may be any according to the specific implementation requirements without thereby abandoning the scope of protection of the following claims. For example, the casing of the writing instrument can be made of metal, a plastic or natural material.

The invention claimed is:

1. A writing instrument, comprising:
   a writing element having a writing end configured for depositing a writing material on a support;
   a plurality of sensors, including:
      a force sensor configured to measure a force applied to said writing element, and
      a movement sensor configured to measure movement of the instrument in a three-dimensional space;
   a communication unit configured to exchange data with a remote device via a wireless communication channel;
   a control unit connected to the plurality of sensors and to the communication unit configured to control the plurality of sensors and the communication unit in order to transmit to the remote device the measurements provided by the plurality of sensors during the connection between the communication unit and the remote device,
   a memory unit connected to the control unit and configured to store one or more measurements of the plurality of sensors, and
   a hollow casing configured to contain at least partially the writing element, so as to leave the writing end of the writing element exposed through a first end of the casing, and to contain completely the plurality of sensors, the control unit, the memory unit and the communication unit,
   wherein the control unit is further configured to:
      detect a first writing measure;
      activate the communication unit when the first writing measure is detected,
      try to establish a connection between the communication unit and the remote device before a maximum time has lapsed from the activation of the communication unit,
      transmit in real time the measurements provided by the plurality of sensors, when the connection is established,
      detect a lack of connection, when the connection is not established within the lapse of the maximum time,
      when there is the lack of connection, detect writing measures corresponding to movement measures having a value greater than a threshold, and
      store the writing measures if, within a predetermined period of time, the control unit detects a number of writing measures greater than a predetermined number.

2. The instrument according to claim 1, wherein the control unit is further configured to transmit in real time the measurements provided by the plurality of sensors only when the control unit detects a number of writing measures greater than the predetermined number.

3. The instrument according to claim 1, wherein the control unit is further configured to:
   activate the communication unit when the first writing measure is detected;
   when a connection is established between the communication unit and the remote device,
   receive a memorization command transmitted by the remote device, and
   store the measurements provided by the plurality of sensors in the memory unit, in response to the reception of the memorization command transmitted by the remote device.

4. The instrument according to claim 1, wherein the control unit is further configured to:
   deactivate the communication unit while storing the measurements provided by the plurality of sensors in the memory unit;
   stop the storage of the measurements in the memory unit when a reduction of the writing measurements below the threshold value is detected, and
   activate the communication unit to exchange data with the remote device.

5. The instrument according to claim 4, wherein the control unit is further configured to:
   deactivate the communication unit when a connection is not established between the communication unit and the remote device before a maximum time has elapsed since the activation of the communication unit;
wait for a waiting period (τ), and
reactivating the communication unit to exchange data with a remote device.

6. The instrument according to claim 1, wherein the control unit is configured to sample at least the measurements provided by the movement sensor with a sampling frequency equal to or greater than 30 Hz.

7. The instrument according to claim 1, wherein the movement sensor is housed in a position closer to a second end of the casing than from the first end of the casing, the second end of the casing being opposite to the first end.

8. The instrument according to claim 1, wherein the movement sensor further comprises:
   a linear acceleration sensor configured to provide a measure of an acceleration of the instrument along a predetermined direction;
   an angular velocity sensor configured to measure a rotation speed of the instrument in a predetermined plane, and
   a magnetometer.

9. The instrument according to claim 1, wherein the casing comprises a separable first portion and a second portion, the first portion and the second portion comprising corresponding mating apertures transverse to a main direction of the casing, wherein the first portion is configured to removably house the writing element and wherein the second portion is configured to house the plurality of sensors, the control unit, the memory unit and the communication unit.

10. The instrument according to claim 9, wherein the second portion of the casing is configured to completely hide the plurality of sensors, the control unit, the memory unit and the communication unit housed therein from a user's view.

11. The instrument according to claim 1, further comprising a power supply unit which can be selectively connected at least to the control unit to provide electric energy thereto, and
   wherein the casing comprises a first portion, a second portion and a third portion which can be separated from one from the other,
   wherein the first portion is configured to removably house at least part of the writing element, the second portion is configured to house the plurality of sensors, the control unit, the memory unit and the communication unit, and the third portion comprises:
      a first element removably fastened to the first portion, and
      a second element removably fastened to the second portion,
   wherein the first element and the second element are slidingly coupled so as to slide between a first position, in which the writing end of the writing element is contained within the first portion, and a second position, in which the first portion and the first element of the third portion move towards the second portion thereby exposing the writing end of the writing element at the first end of the casing, and
   wherein the first element comprises a conductive component configured to contact a pair of electrical contacts connected to the power supply unit and protruding from the second portion towards the first element of the third portion, when the first element and the second element are in the second position, the contact between the pair of electrical contacts and the conductive component allowing the supply of electrical energy at least to the control unit.

12. The instrument according to claim 11, wherein the second element of the third portion further comprises:
   a coupling end to the second portion,
   a free end opposite the coupling end,
   a through hole between the free end and the coupling end, the through hole being shaped to receive the writing element and to hold a terminal end of the writing element, opposite the writing end, at the coupling end, and
   at least one pin projecting in a direction transverse to the length direction of the through hole,
   wherein the first element of the third portion further comprises:
      a coupling end to the first portion,
      a free end opposite the coupling end,
      a through hole between the free end and the coupling end, the through hole being configured to at least partially receive the second element of the third portion,
      a helical groove formed in a wall that delimits the through hole, the groove being adapted to receive the pin of the second element so as to guide a rotation of the first element with respect to the second element during the sliding between the first position and the second position, and vice versa, and
      a shoulder portion at the free end and facing the second portion, the shoulder portion being configured to house the conductive component.

13. The instrument according to claim 12, wherein the conductive component comprises a sheet of electrically conductive material and wherein the electrical contacts are of the pogo pin type.

14. The instrument according to claim 1, wherein the writing element is one of:
   an ink pen refill;
   a core of an infinite pencil;
   a core of a pop-a-point pencil, and
   a stick made in porous material soaked in ink.

15. A system for monitoring and analyzing handwriting, comprising a writing instrument and a processing device,
   wherein the writing instrument comprises:
      a writing element comprising a writing end configured for depositing a writing material on a support;
      a plurality of sensors, including:
         a force sensor configured to measure a force applied to said writing element, and
         a movement sensor configured to measure movement of the instrument in a three-dimensional space;
      a communication unit configured to exchange data with a remote device via a wireless communication channel;
      a control unit connected to the plurality of sensors and to the communication unit configured to control the plurality of sensors and the communication unit in order to transmit to the remote device the measurements provided by the plurality of sensors during the connection between the communication unit and the remote device,
      a memory unit connected to the control unit and configured to store one or more measurements of the plurality of sensors, and
      a hollow casing configured to contain at least partially the writing element, so as to leave the writing end of the writing element exposed through a first end of the casing, and to contain completely the plurality of sensors, the control unit, the memory unit and the communication unit, wherein the control unit is further configured to:
  detect a first writing measure;
  activate the communication unit when the first writing measure is detected,
  try to establish a connection between the communication unit and the remote device before a maximum time has lapsed from the activation of the communication unit,
  transmit in real time the measurements provided by the plurality of sensors, when the connection is established,
  detect a lack of connection, when the connection is not established within the lapse of the maximum time,
  when there is the lack of connection, detect writing measures corresponding to movement measures having a value greater than a threshold, and
  store the writing measures if, within a predetermined period of time, the control unit detects a number of writing measures greater than a predetermined number, and wherein the processing device comprises:
  a communication module configured to exchange data with the communication unit of the writing instrument, and
  a processing module configured to process the data provided by the writing instrument and providing an indication relating to at least one symbol written with the writing instrument.

16. A writing analysis method, implemented by a system for monitoring and analyzing handwriting, comprising a writing instrument and a processing device, wherein the writing instrument comprises:
  a writing element comprising a writing end configured for depositing a writing material on a support;
  a plurality of sensors, including:
    a force sensor configured to measure a force applied to said writing element, and
    a movement sensor configured to measure movement of the instrument in a three-dimensional space;
  a communication unit configured to exchange data with a remote device via a wireless communication channel;
  a control unit connected to the plurality of sensors and to the communication unit configured to control the plurality of sensors and the communication unit in order to transmit to the remote device the measurements provided by the plurality of sensors during the connection between the communication unit and the remote device,
  a memory unit connected to the control unit and configured to store one or more measurements of the plurality of sensors, and
  a hollow casing configured to contain at least partially the writing element, so as to leave the writing end of the writing element exposed through a first end of the casing, and to contain completely the plurality of sensors, the control unit, the memory unit and the communication unit, wherein the control unit is further configured to:
  detect a first writing measure;
  activate the communication unit when the first writing measure is detected,
  try to establish a connection between the communication unit and the remote device before a maximum time has lapsed from the activation of the communication unit,
  transmit in real time the measurements provided by the plurality of sensors, when the connection is established,
  detect a lack of connection, when the connection is not established within the lapse of the maximum time,
  when there is the lack of connection, detect writing measures corresponding to movement measures having a value greater than a threshold, and
  store the writing measures if, within a predetermined period of time, the control unit detects a number of writing measures greater than a predetermined number, and wherein the processing device comprises:
  a communication module configured to exchange data with the communication unit of the writing instrument, and
  a processing module configured to process the data provided by the writing instrument and providing an indication relating to at least one symbol written with the writing instrument, the method comprising the steps of:
    determining a static disturbance in the force measures provided by the force sensor of the plurality of sensors of the writing instrument;
    subtracting the static disturbance from the force measures provided by the force sensor;
    processing the force measures provided by the force sensor by means of an algorithm for estimating and removing a baseline;
    converting to a null value, each measured value lower than a threshold value; and
    identifying a sequence of force measures different from zero as a single continuous writing movement performed through the writing instrument.

17. The method according to claim 16, further comprising the steps of:
  determining a variation frequency of the movement measures provided by the movement sensor, and
  when said variation frequency is greater than a threshold value:
    calculating a tilt angular velocity of the writing instrument on the basis of angular velocity measures included in the movement measures provided by the movement sensor;
    calculating a further tilt angular velocity of the writing instrument on the basis of linear acceleration measures included in the measures of movement provided by the movement sensor, and
    calculating an adjusted tilt angular velocity of the writing instrument as a linear combination of the tilt angular velocity and of the further tilt angular velocity of the writing instrument.

18. The method according to claim 17, wherein the step of calculating an adjusted tilt angular velocity of the writing instrument as a linear combination of the tilt angular velocity and of the further tilt angular velocity of the writing instrument further comprises calculating the adjusted tilt angular velocity as:

$$\hat{\vartheta}=k_1\hat{\vartheta}_g+k_2(\hat{\vartheta}_a-\hat{\vartheta}),$$

where $\hat{\vartheta}_g$ is the tilt angular velocity determined on the basis of angular velocity measures, $\hat{\vartheta}_a$ is the tilt angle determined based on the further tilt angular velocity of the writing instrument based on the linear acceleration measures, $k_1$ is a constant parameter comprised between 1.2 and 1.7, and $k_2$ is a constant parameter comprised between 0.3 and 0.6.

19. The method according to claim 17, further comprising, when the variation frequency is equal to and less than the threshold value calculating the tilt angle of the writing instrument as:

$$\vartheta = \sin^{-1}\left(\frac{a_z}{g}\right),$$

where $a_2$ is an acceleration measure aligned to a main direction of the writing instrument and g is the acceleration of gravity.

* * * * *